United States Patent
Hart et al.

(10) Patent No.: US 10,053,963 B2
(45) Date of Patent: Aug. 21, 2018

(54) EXPANDABLE DEVICE FOR USE IN A WELL BORE

(71) Applicant: Halliburton Energy Services, Inc., Houston, TX (US)

(72) Inventors: Barrie Hart, Ipswich (GB); Craig D. Johnson, Montgomery, TX (US); L. McDonald Schetky, Camden, ME (US); Peter Besselink, Enschede (NL)

(73) Assignee: Halliburton Energy Services, Inc., Houston, TX (US)

( * ) Notice: Subject to any disclaimer, the term of this patent is extended or adjusted under 35 U.S.C. 154(b) by 734 days.

(21) Appl. No.: 14/291,324

(22) Filed: May 30, 2014

(65) Prior Publication Data

US 2014/0299331 A1    Oct. 9, 2014

Related U.S. Application Data

(60) Division of application No. 13/729,550, filed on Dec. 28, 2012, now Pat. No. 8,776,876, which is a
(Continued)

(51) Int. Cl.
| | |
|---|---|
| *E21B 43/10* | (2006.01) |
| *E21B 23/06* | (2006.01) |
| *E21B 43/08* | (2006.01) |
| *A61F 2/91* | (2013.01) |
| *E21B 33/12* | (2006.01) |

(Continued)

(52) U.S. Cl.
CPC ............ *E21B 43/103* (2013.01); *E21B 23/06* (2013.01); *E21B 43/086* (2013.01); *E21B 43/106* (2013.01); *E21B 43/108* (2013.01); *A61F 2/91* (2013.01); *E21B 33/124* (2013.01); *E21B 33/1208* (2013.01); *E21B 33/1277* (2013.01); *E21B 41/02* (2013.01); *E21B 43/105* (2013.01); *E21B 43/164* (2013.01)

(58) Field of Classification Search
CPC ...... E21B 23/06; E21B 43/103; E21B 43/106; E21B 43/108
See application file for complete search history.

(56) References Cited

U.S. PATENT DOCUMENTS

| | | | |
|---|---|---|---|
| 5,695,516 A | 12/1997 | Fischell et al. | |
| 5,901,789 A * | 5/1999 | Donnelly | E21B 43/04 166/207 |

(Continued)

FOREIGN PATENT DOCUMENTS

WO    9849423 A1    11/1998

OTHER PUBLICATIONS

Shell Canada Limited. WO 93/25800. Published Dec. 23, 1993.*
(Continued)

*Primary Examiner* — Nicole Coy
*Assistant Examiner* — Tara E Schimpf
(74) *Attorney, Agent, or Firm* — McDermott Will & Emery LLP

(57) ABSTRACT

An expandable device comprising a plurality of expandable cells. The cells may be bistable cells or other types of cells that are expanded from a contracted position towards an expanded position. Additionally, the cells may be combined with locking mechanisms to hold the structure in an expanded position.

17 Claims, 33 Drawing Sheets

Related U.S. Application Data continuation of application No. 13/431,265, filed on Mar. 27, 2012, now Pat. No. 8,397,804, which is a division of application No. 12/856,241, filed on Aug. 13, 2010, now Pat. No. 8,230,913, which is a continuation of application No. 11/150,836, filed on Jun. 10, 2005, which is a continuation of application No. 10/050,468, filed on Jan. 16, 2002.

(60) Provisional application No. 60/296,875, filed on Jun. 8, 2001, provisional application No. 60/261,749, filed on Jan. 16, 2001.

(51) Int. Cl.
*E21B 33/124* (2006.01)
*E21B 33/127* (2006.01)
*E21B 41/02* (2006.01)
*E21B 43/16* (2006.01)

(56) References Cited

U.S. PATENT DOCUMENTS

| | | | |
|---|---|---|---|
| 5,924,745 A | 7/1999 | Campbell | |
| 6,273,634 B1* | 8/2001 | Lohbeck | E21B 17/08 |
| | | | 166/207 |
| 6,799,637 B2* | 10/2004 | Schetky | E21B 23/00 |
| | | | 166/207 |
| 8,776,876 B2 | 7/2014 | Hart et al. | |
| 2002/0046840 A1* | 4/2002 | Schetky | E21B 23/00 |
| | | | 166/277 |

OTHER PUBLICATIONS

Official Action for Canadian Application No. 2,745,733 dated Mar. 21, 2014.
Official Action for Norwegian Patent Application No. 20140642 dated Feb. 11, 2016.

* cited by examiner

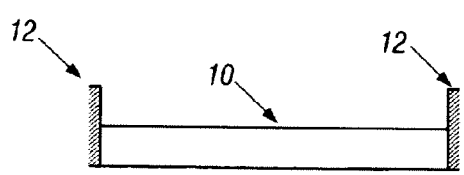
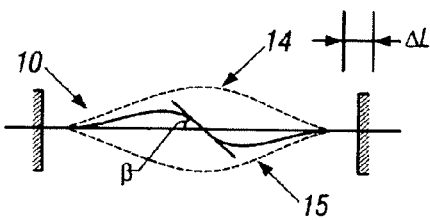
FIG. 1A
FIG. 1B
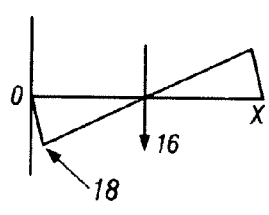
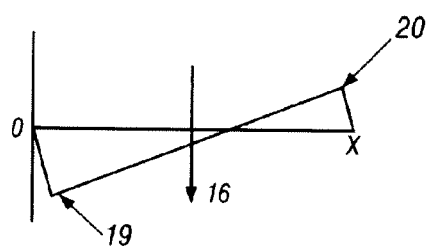
FIG. 2A
FIG. 2B
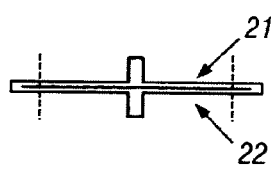
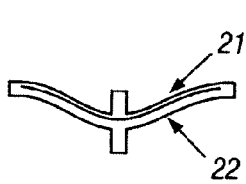
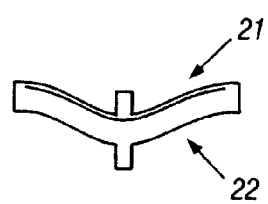
FIG. 3A
FIG. 3B
FIG. 3C
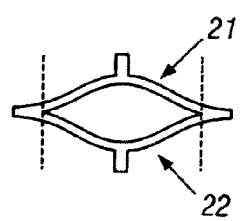
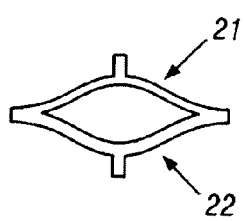
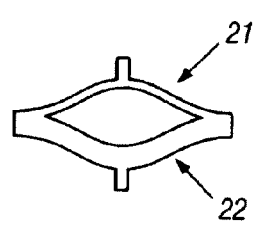
FIG. 3D
FIG. 3E
FIG. 3F

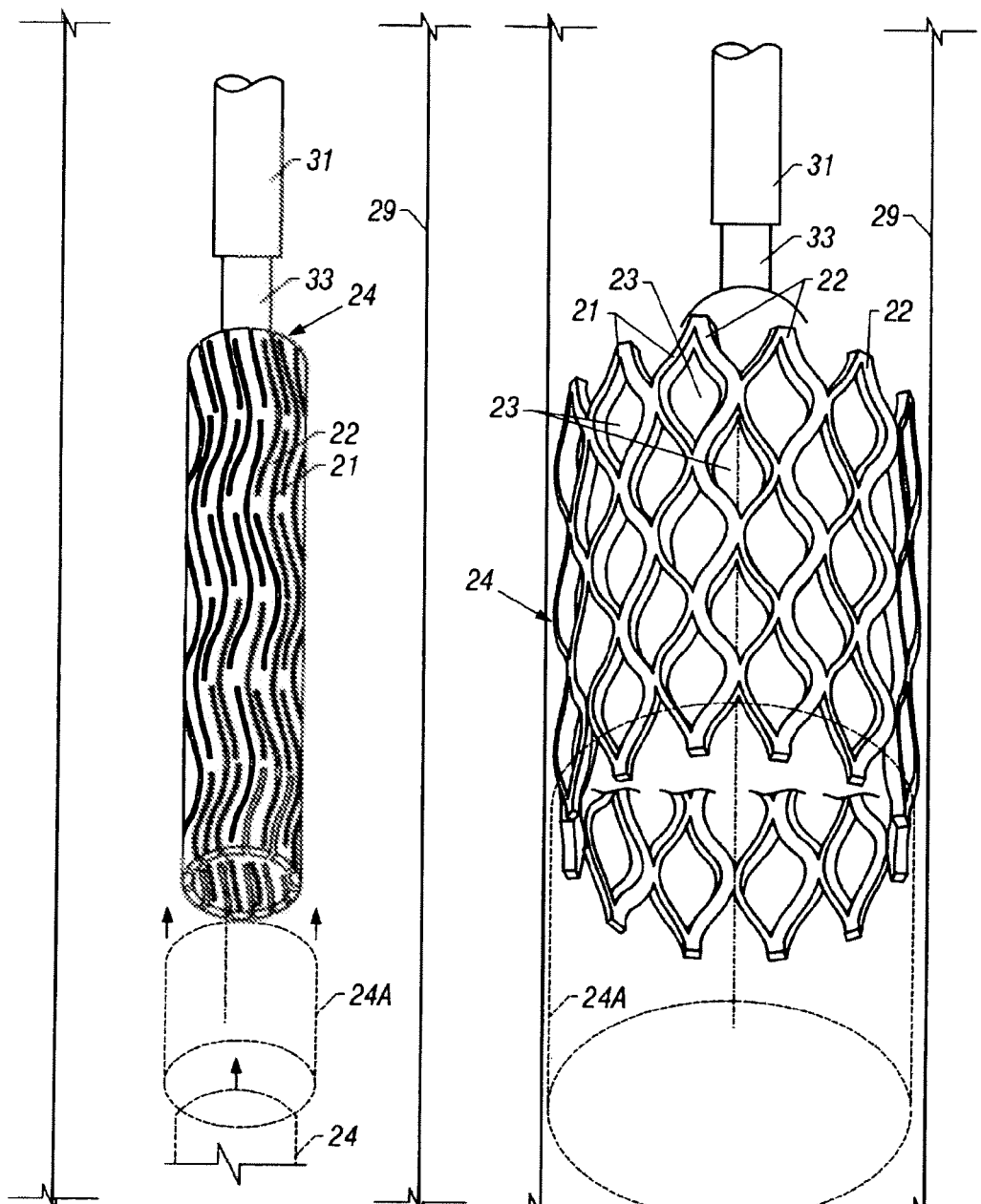
*FIG. 4C*     *FIG. 4D*

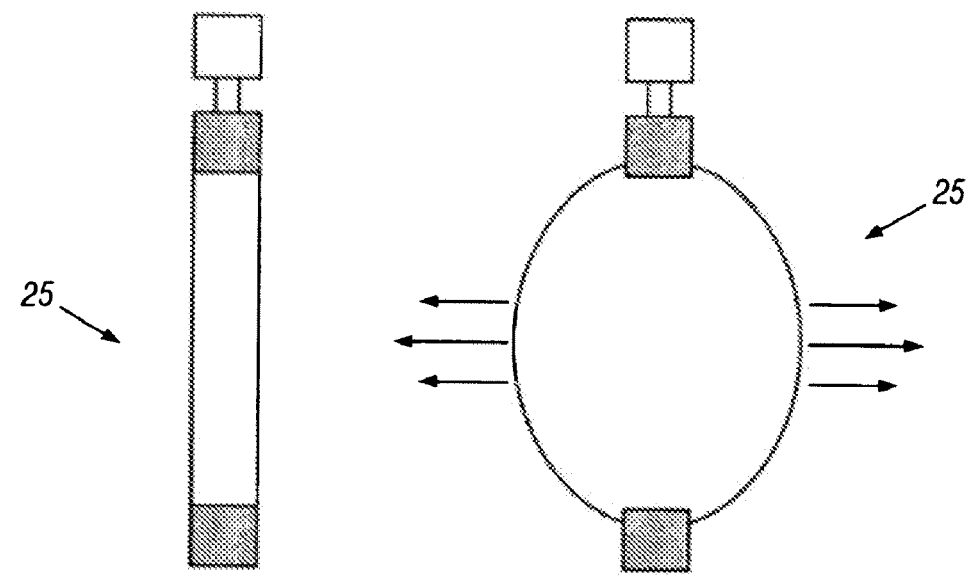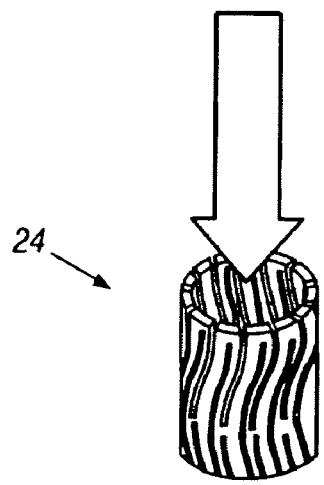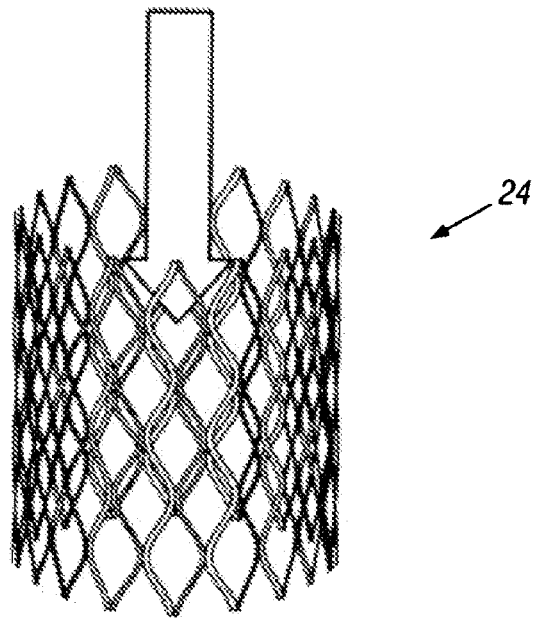
*FIG. 5A*  *FIG. 5B*

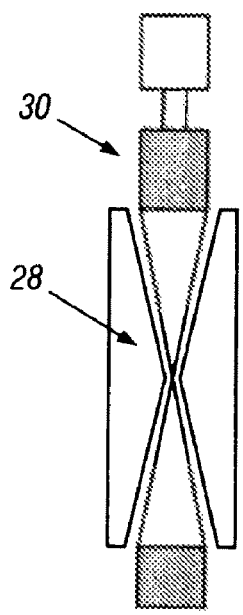
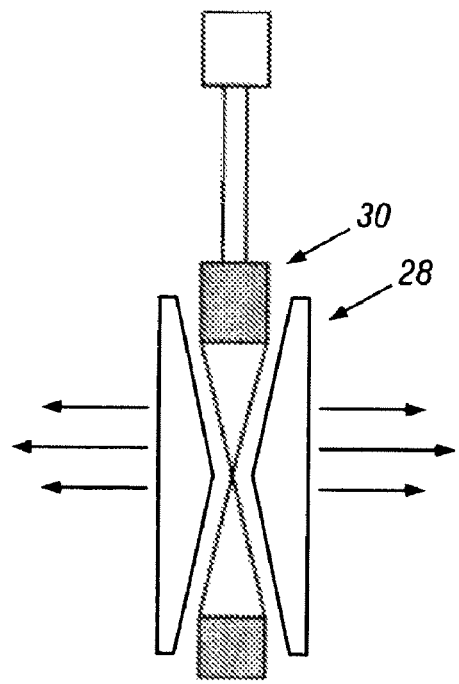
FIG. 7A          FIG. 7B
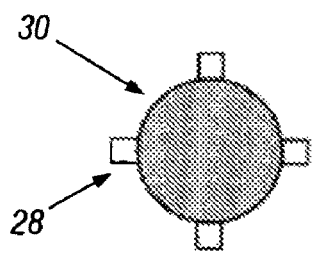
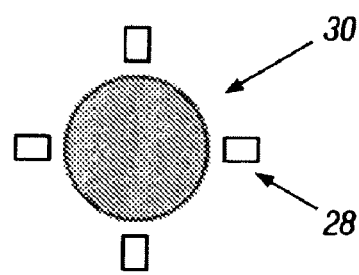
FIG. 7C          FIG. 7D

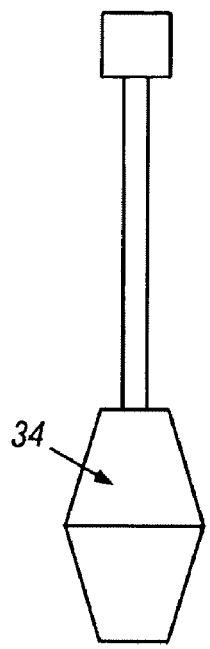
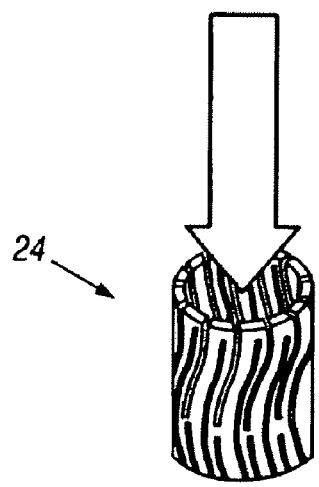
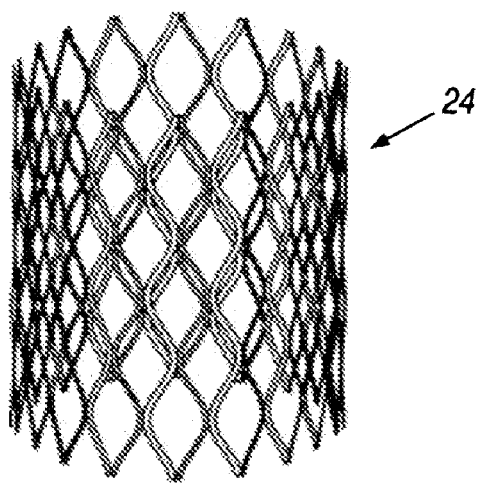
FIG. 9A    FIG. 9B

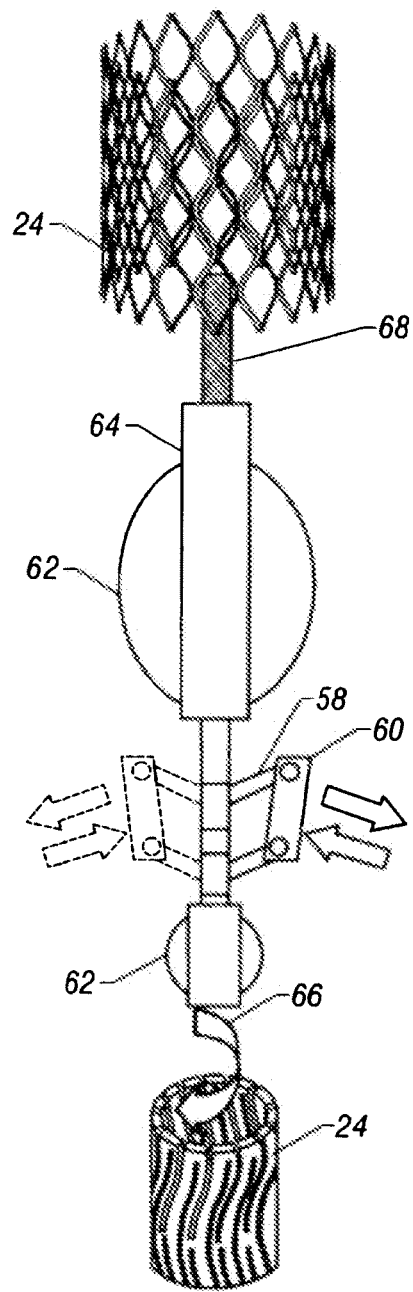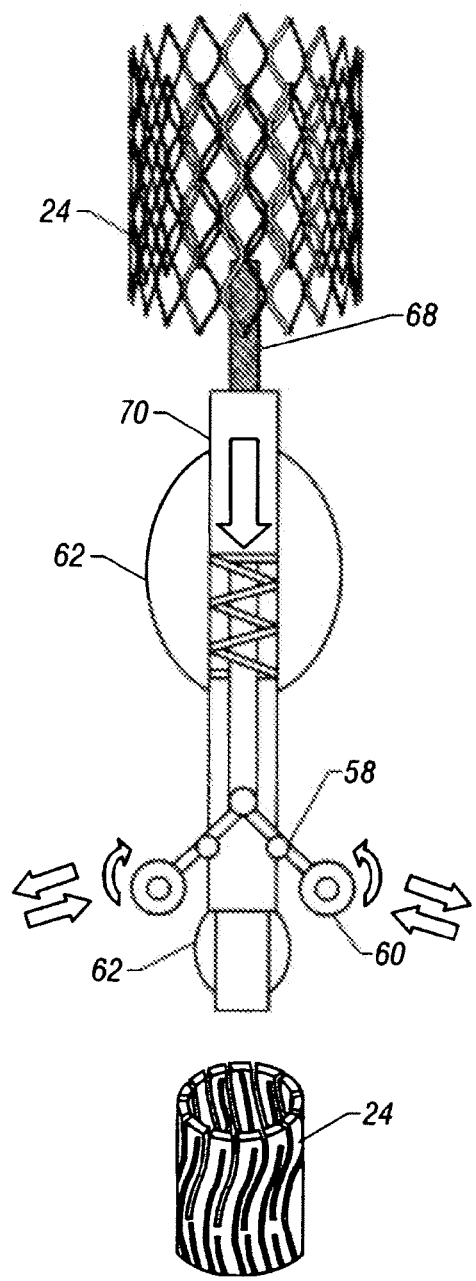
*FIG. 12*  *FIG. 13*

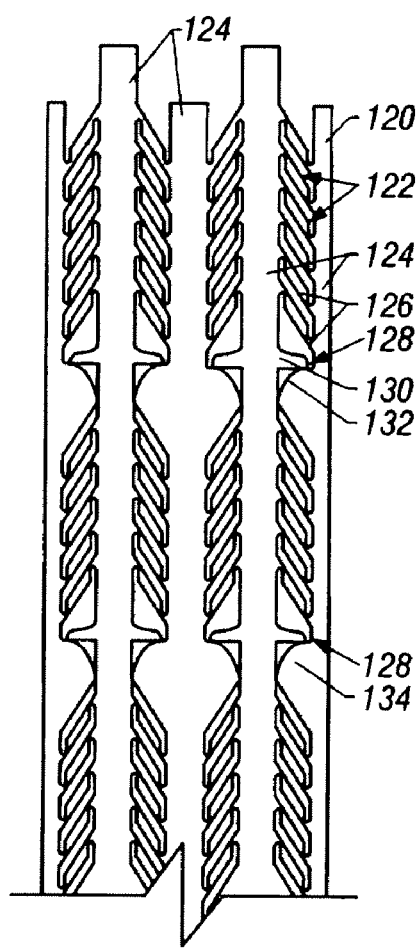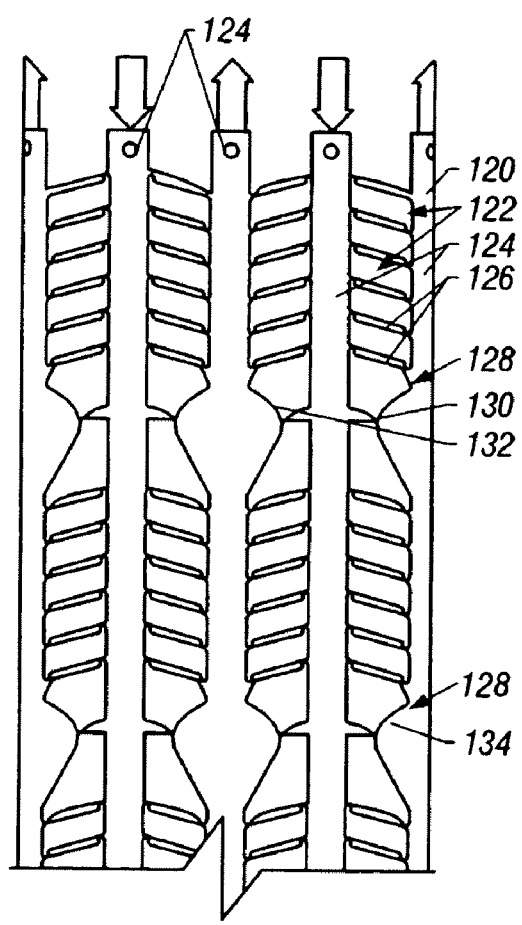
*FIG. 22A*          *FIG. 22B*

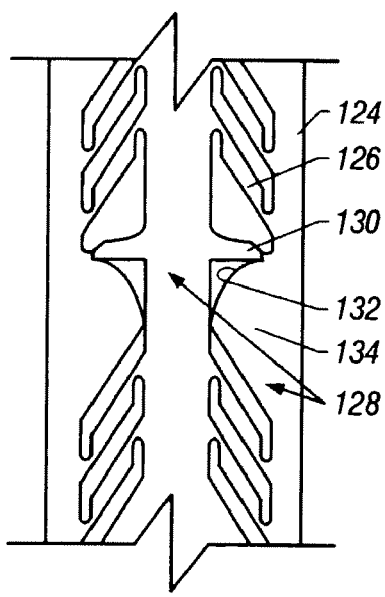 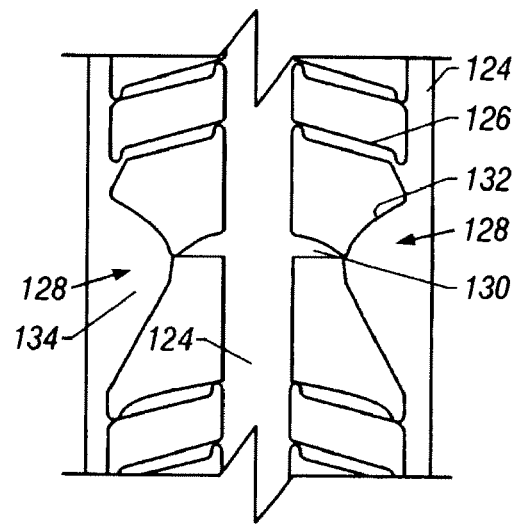
FIG. 23A            FIG. 23B

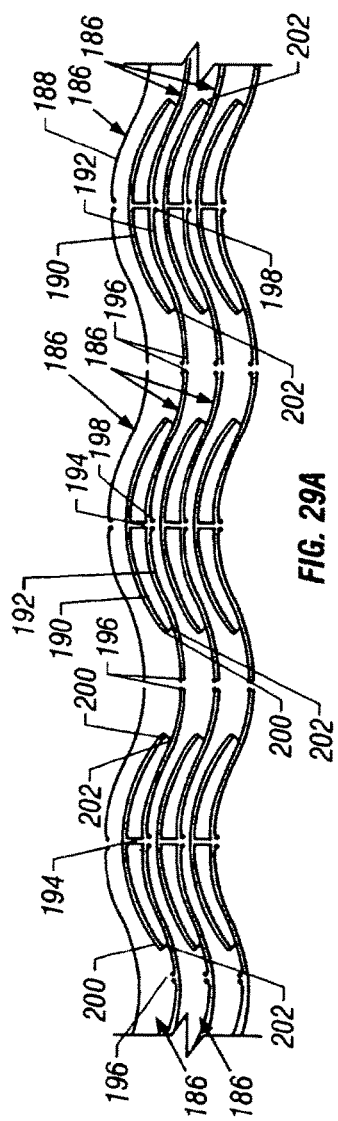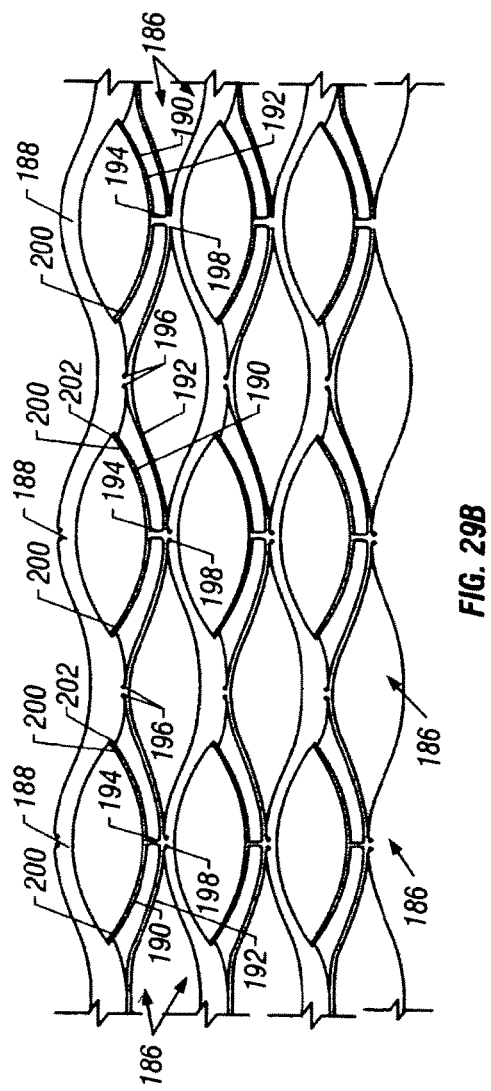
FIG. 29A
FIG. 29B

EXPANDABLE DEVICE FOR USE IN A WELL BORE

CROSS-REFERENCE TO RELATED APPLICATIONS

This application is a divisional of U.S. application Ser. No. 13/729,550 filed on Dec. 28, 2012, which is a continuation of U.S. Ser. No. 13/431,265 filed Mar. 27, 2012 and now U.S. Pat. No. 8,397,804, which is a divisional of U.S. application Ser. No. 12/856,241 filed on Aug. 13, 2010 and now U.S. Pat. No. 8,230,913, which is a continuation of U.S. application Ser. No. 11/150,836, filed Jun. 10, 2005 and now abandoned, which is a continuation of application Ser. No. 10/050,468 filed Jan. 16, 2002 and now abandoned, which claims the benefit of priority to U.S. Provisional Application No. 60/261,749 filed Jan. 16, 2001 and U.S. Provisional Application No. 60/296,875 filed Jun. 8, 2001, which applications are incorporated herein by reference.

FIELD OF THE INVENTION

This invention relates generally to expandable devices, and particularly to devices formed from one or more expandable cells that facilitate transition of the device from a contracted state to an expanded state.

BACKGROUND OF THE INVENTION

In a variety of applications and environments, it would be beneficial to have a device able to transition from a contracted state to an expanded state. Such devices can comprise planar members, tubular members, rectangular members and a variety of other configurations. Exemplary applications include medical applications in which expandable devices, such as stents, are deployed at a desired location and then expanded. Another exemplary application comprises the use of expandables in the retrieval of various fluids, e.g. oil, from subterranean locations.

For example, fluids such as oil, natural gas and water are obtained from subterranean geologic formations (a "reservoir") by drilling a well that penetrates the fluid-bearing formation. Once a wellbore has been drilled to a certain depth, the borehole wall typically is supported to prevent collapse. During the drilling and use of a wellbore, various tubular members, such as liners, casings, sandscreens, etc. are deployed within the wellbore.

Various methods have been developed for radially expanding tubulars by, for instance, pulling an expansion mandrel through the tubular to plastically deform the tubular in a radially outward direction. Such an approach, however, requires a large amount of force to achieve the desired expansion.

The medical industry, oil industry and a variety of other industries utilize certain types of expandables or would benefit from the use of expandables in numerous applications. However, there are very few existing devices that are readily expandable at a desired location. Of the devices that do exist, substantial forces are required to create the expansion. Also, substantial plastic deformation often occurs which can limit the selection of available materials for a given expandable device. The present invention is directed to overcoming, or at least reducing, the effects of one or more of the problems set forth above.

SUMMARY OF THE INVENTION

The present invention relates generally to expandable devices that may be used, for example, in subterranean environments. In one embodiment of the invention, the expandable device comprises one or more expandable cells that facilitate expansion of the device. By way of example, a tubular may be formed with a plurality of expandable cells that facilitate radial expansion of the device from a collapsed or contracted state to an expanded state. A variety of cell types and cell designs may be utilized depending on the application and desired parameters of the expandable device.

BRIEF DESCRIPTION OF THE DRAWINGS

The invention will hereafter be described with reference to the accompanying drawings, wherein like reference numerals denote like elements, and:

FIGS. 1A and 1B are illustrations of the forces imposed to make a bistable structure;

FIGS. 2A and 2B show force-deflection curves of two bistable structures;

FIGS. 3A-3F illustrate expanded and collapsed states of three bistable cells with various thickness ratios;

FIGS. 4C and 4D illustrate a bistable expandable tubular in collapsed and expanded states within a wellbore;

FIGS. 5A and 5B illustrate an expandable packer type of deployment device;

FIGS. 7A-7D illustrate an expandable swage type of deployment device;

FIGS. 9A and 9B illustrate a plug type of deployment device;

FIG. 12 illustrates a motor driven radial roller deployment device;

FIG. 13 illustrates a hydraulically driven radial roller deployment device;

FIGS. 22 A-B are partial side elevational view of an embodiment of the present invention in the contracted and expanded positions respectively;

FIGS. 23 A-B are partial side elevational views of an embodiment of the present invention in the contracted and expanded positions respectively;

FIGS. 29 A-B illustrate another embodiment of expandable cells displayed in their contracted and expanded positions, respectively;

Figure 4A:
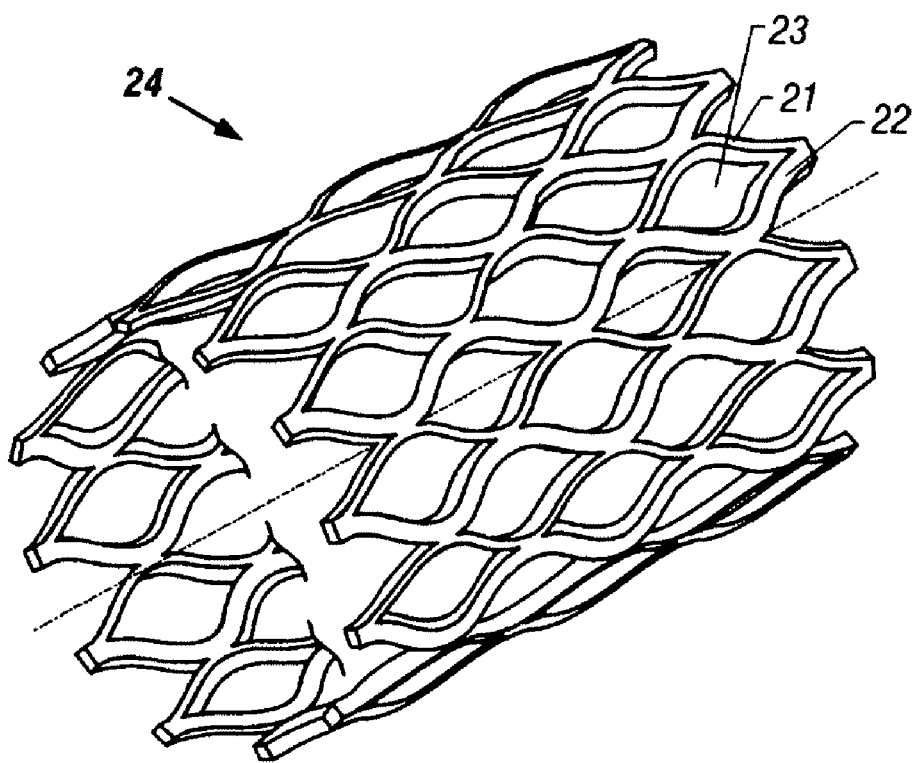
FIGS. 4A and 4B illustrate a bistable expandable tubular in its expanded and collapsed states.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION

The following describes a variety of expandable devices that utilize expandable cells to facilitate expansion of the device from a contracted state to an expanded state. Various expansion techniques, expandable cell designs, and locking mechanisms are described, and typically the description is related to one or more exemplary applications. For example, the cells are described for use in tubular components, such as tubulars used in the oil production industry. However, this application is only an exemplary application to demonstrate the applicability of the various cells and locking mechanisms described herein. The description should not be construed as limiting the application of such expandable devices to the particular environments or applications described herein. Rather the techniques for formulating expandable devices can have a wide range of applications in other environments and industries.

As described below, exemplary expandable devices may or may not comprise bistable cells. Whether bistable or not, the expandable cells facilitate expansion of a given device between a contracted state and an expanded state for a variety of operations or procedures. The selection of a particular type of expandable cell depends on a variety of factors including environment, degree of expansion, materials available, etc.

Bistable devices used in the present invention can take advantage of a principle illustrated in FIGS. 1A and 1B. FIG. 1A shows a rod 10 fixed at each end to rigid supports 12. If the rod 10 is subjected to an axial force it begins to deform as shown in FIG. 1B. As the axial force is increased rod 10 ultimately reaches its Euler buckling limit and deflects to one of the two stable positions shown as 14 and 15. If the buckled rod is now clamped in the buckled position, a force at right angles to the long axis can cause the rod to move to either of the stable positions but to no other position. When the rod is subjected to a lateral force it must move through an angle .beta. before deflecting to its new stable position.

Bistable systems are characterized by a force deflection curve such as those shown in FIGS. 2A and 2B. The externally applied force 16 causes the rod 10 of FIG. 1B to move in the direction X and reaches a maximum 18 at the onset of shifting from one stable configuration to the other. Further deflection requires less force because the system now has a negative spring rate and when the force becomes zero the deflection to the second stable position is spontaneous.

The force deflection curve for this example is symmetrical and is illustrated in FIG. 2A. By introducing either a precurvature to the rod or an asymmetric cross section the force deflection curve can be made asymmetric as shown in FIG. 2B. In this system the force 19 required to cause the rod to assume one stable position is greater than the force 20 required to cause the reverse deflection. The force 20 must be greater than zero for the system to have bistable characteristics.

Bistable structures, sometimes referred to as toggle devices, have been used in industry for such devices as flexible discs, over center clamps, hold-down devices and quick release systems for tension cables (such as in sailboat rigging backstays).

Instead of using the rigid supports as shown in FIGS. 1A and 1B, a cell can be constructed where the restraint is provided by curved struts connected at each end as shown in FIGS. 3A-3F. If both struts 21 and 22 have the same thickness as shown in FIGS. 3A and 3B, the force deflection curve is linear and the cell lengthens when compressed from its open position FIG. 3B to its closed position FIG. 3A. If the cell struts have different thicknesses, as shown in FIGS. 3C-3F, the cell has the force deflection characteristics shown in FIG. 2B, and does not change in length when it moves between its two stable positions. An expandable bistable tubular can thus be designed so that as the radial dimension expands, the axial length remains constant. In one example, if the thickness ratio is over approximately 2:1, the heavier strut resists longitudinal changes. By changing the ratio of thick-to-thin strut dimensions, the opening and closing forces can be changed. For example, FIGS. 3C and 3D illustrate a thickness ratio of approximately 3:1, and FIGS. 3E and 3F illustrate a thickness ratio of approximately 6:1.

Figure 4B:
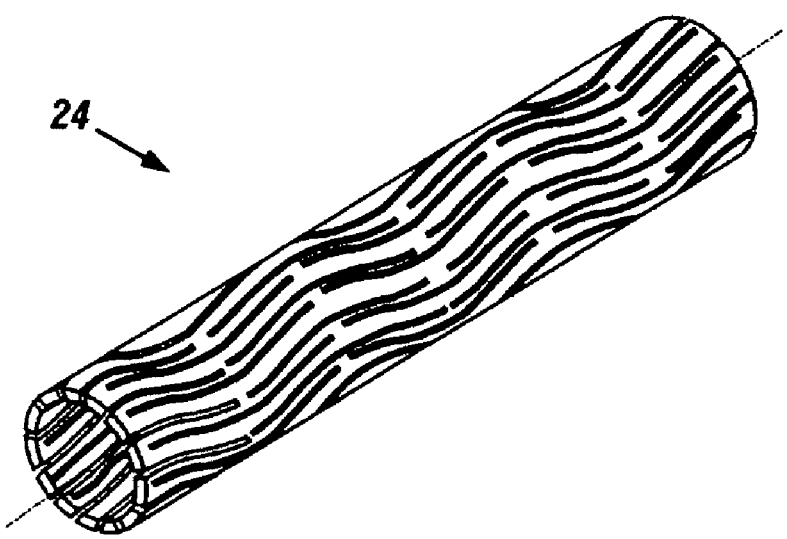

An expandable bore bistable tubular, such as casing, a tube, a patch, or pipe, can be constructed with a series of circumferential bistable connected cells 23 as shown in FIGS. 4A and 4B, where each thin strut 21 is connected to a thick strut 22. The longitudinal flexibility of such a tubular can be modified by changing the length of the cells and by connecting each row of cells with a compliant link. Further, the force deflection characteristics and the longitudinal flexibility can also be altered by the design of the cell shape. FIG. 4A illustrates an expandable bistable tubular 24 in its expanded configuration while FIG. 4B illustrates the expandable bistable tubular 24 in its contracted or collapsed configuration. Within this application the term "collapsed" is used to identify the configuration of the bistable element or device in the stable state with the smallest diameter, it is not meant to imply that the element or device is damaged in any way. In the collapsed state, bistable tubular 24 is readily introduced into a wellbore 29, as illustrated in FIG. 4C. Upon placement of the bistable tubular 24 at a desired wellbore location, it is expanded, as illustrated in FIG. 4D.

The geometry of the bistable cells is such that the tubular cross-section can be expanded in the radial direction to increase the overall diameter of the tubular. As the tubular expands radially, the bistable cells deform elastically until a specific geometry is reached. At this point the bistable cells move, e.g. snap, to a final expanded geometry. With some materials and/or bistable cell designs, enough energy can be released in the elastic deformation of the cell (as each bistable cell snaps past the specific geometry) that the expanding cells are able to initiate the expansion of adjoining bistable cells past the critical bistable cell geometry. Depending on the deflection curves, a portion or even an entire length of bistable expandable tubular can be expanded from a single point.

In like manner if radial compressive forces are exerted on an expanded bistable tubular, it contracts radially and the bistable cells deform elastically until a critical geometry is reached. At this point the bistable cells snap to a final collapsed structure. In this way the expansion of the bistable tubular is reversible and repeatable. Therefore the bistable tubular can be a reusable tool that is selectively changed between the expanded state as shown in FIG. 4A and the collapsed state as shown in FIG. 4B.

In the collapsed state, as in FIG. 4B, the bistable expandable tubular is easily inserted into the wellbore and placed into position. A deployment device is then used to change the configuration from the collapsed state to the expanded state.

In the expanded state, as in FIG. 4A, design control of the elastic material properties of each bistable cell can be such that a constant radial force can be applied by the tubular wall to the constraining wellbore surface. The material properties and the geometric shape of the bistable cells can be designed to give certain desired results.

Figure 11:
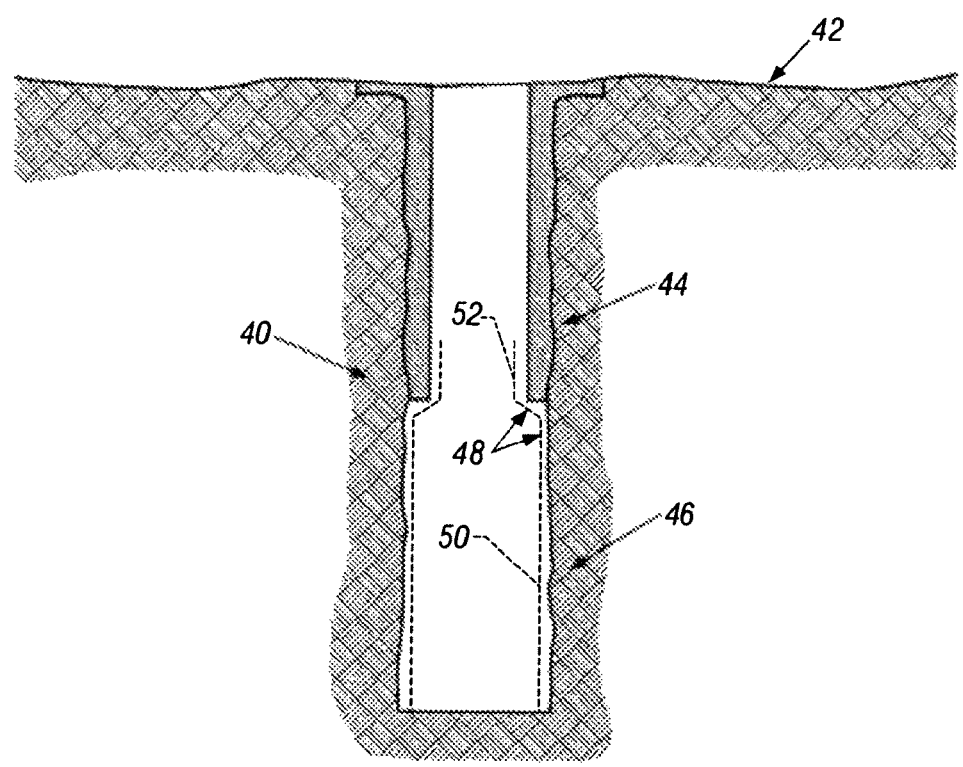
FIG. 11 is a schematic of a wellbore utilizing an expandable bistable tubular.

One example of designing for certain desired results is an expandable bistable tubular string with more than one diameter throughout the length of the string. This can be useful in boreholes with varying diameters, whether designed that way or as a result of unplanned occurrences such as formation washouts or keyseats within the borehole. This also can be beneficial when it is desired to have a portion of the bistable expandable device located inside a cased section of the well while another portion is located in an uncased section of the well. FIG. 11 illustrates one example of this condition. A wellbore 40 is drilled from the surface 42 and comprises a cased section 44 and an openhole section 46. An expandable bistable device 48 having segments 50, 52 with various diameters is placed in the well. The segment with a larger diameter 50 is used to stabilize the openhole section 46 of the well, while the segment having a reduced diameter 52 is located inside the cased section 44 of the well.

Bistable collars or connectors 24 A (see FIG. 4C) can be designed to allow sections of the bistable expandable tubular to be joined together into a string of useful lengths using the same principle as illustrated in FIGS. 4A and 4B. This bistable connector 24 A also incorporates a bistable cell design that allows it to expand radially using the same mechanism as for the bistable expandable tubular component. Exemplary bistable connectors have a diameter slightly larger than the expandable tubular sections that are being joined. The bistable connector is then placed over the ends of the two sections and mechanically attached to the expandable tubular sections. Mechanical fasteners such as screws, rivets or bands can be used to connect the connector to the tubular sections. The bistable connector typically is designed to have an expansion rate that is compatible with the expandable tubular sections, so that it continues to connect the two sections after the expansion of the two segments and the connector.

Alternatively, the bistable connector can have a diameter smaller than the two expandable tubular sections joined. Then, the connector is inserted inside of the ends of the tubulars and mechanically fastened as discussed above. Another embodiment would involve the machining of the ends of the tubular sections on either their inner or outer surfaces to form an annular recess in which the connector is located. A connector designed to fit into the recess is placed in the recess. The connector would then be mechanically attached to the ends as described above. In this way the connector forms a relatively flush-type connection with the tubular sections.

A conveyance device 31 transports the bistable expandable tubular lengths and bistable connectors into the wellbore and to the correct position. (See FIGS. 4C and 4D). The conveyance device may utilize one or more mechanisms such as wireline cable, coiled tubing, coiled tubing with wireline conductor, drill pipe, tubing or casing.

A deployment device 33 can be incorporated into the overall assembly to expand the bistable expandable tubular and connectors. (See FIGS. 4C and 4D). Deployment devices can be of numerous types such as an inflatable packer element, a mechanical packer element, an expandable swage, a piston apparatus, a mechanical actuator, an electrical solenoid, a plug type apparatus, e.g. a conically shaped device pulled or pushed through the tubing, a ball type apparatus or a rotary type expander as further discussed below.

An inflatable packer element is shown in FIGS. 5A and 5B and is a device with an inflatable bladder, element, or bellows incorporated into the bistable expandable tubular system bottom hole assembly. In the illustration of FIG. 5A, the inflatable packer element 25 is located inside the entire length, or a portion, of the initial collapsed state bistable tubular 24 and any bistable expandable connectors (not shown). Once the bistable expandable tubular system is at the correct deployment depth, the inflatable packer element 25 is expanded radially by pumping fluid into the device as shown in FIG. 5B. The inflation fluid can be pumped from the surface through tubing or drill pipe, a mechanical pump, or via a downhole electrical pump which is powered via wireline cable. As the inflatable packer element 25 expands, it forces the bistable expandable tubular 24 to also expand radially. At a certain expansion diameter, the inflatable packer element causes the bistable cells in the tubular to reach a critical geometry where the bistable "snap" effect is initiated, and the bistable expandable tubular system expands to its final diameter. Finally the inflatable packer element 25 is deflated and removed from the deployed bistable expandable tubular 24.

Figures 6A, 6B:
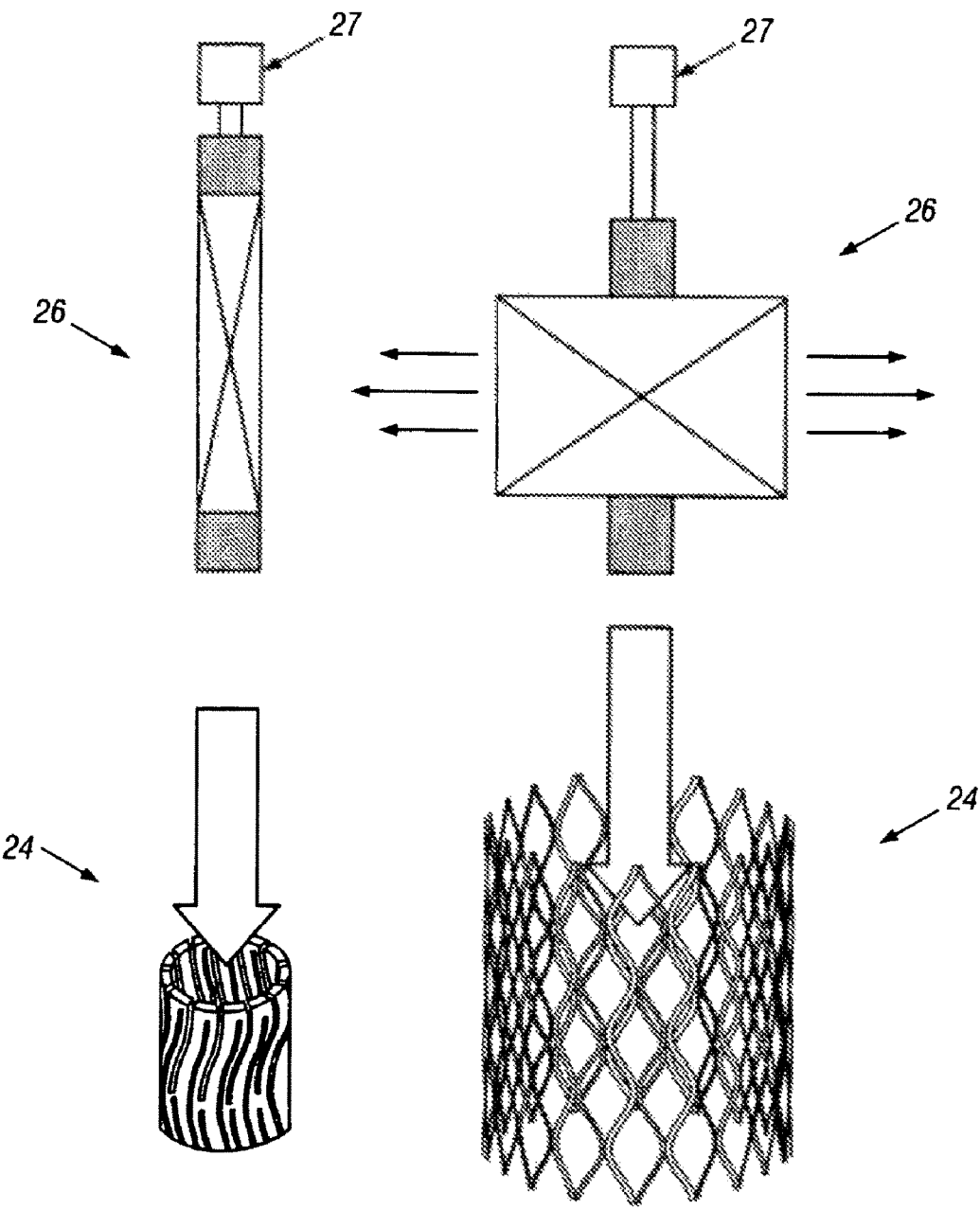
FIGS. 6A and 6B illustrate a mechanical packer type of deployment device.

A mechanical packer element is shown in FIGS. 6A and 6B and is a device with a deformable plastic element 26 that expands radially when compressed in the axial direction. The force to compress the element can be provided through a compression mechanism 27, such as a screw mechanism, cam, or a hydraulic piston. The mechanical packer element deploys the bistable expandable tubulars and connectors in the same way as the inflatable packer element. The deformable plastic element 26 applies an outward radial force to the inner circumference of the bistable expandable tubulars and connectors, allowing them in turn to expand from a contracted position (see FIG. 6A) to a final deployment diameter (see FIG. 6B).

An expandable swage is shown in FIGS. 7A-7D and comprises a series of fingers 28 that are arranged radially around a conical mandrel 30. FIGS. 7A and 7C show side and top views respectively. When the mandrel 30 is pushed or pulled through the fingers 28 they expand radially outwards, as illustrated in FIGS. 7B and 7D. An expandable swage is used in the same manner as a mechanical packer element to deploy a bistable expandable tubular and connector.

Figure 8A:
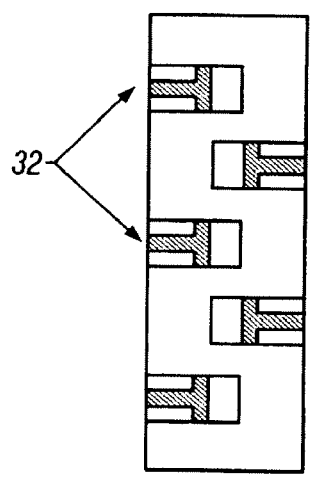
FIGS. 8A-8D illustrate a piston type of deployment device.
Figure 8B:
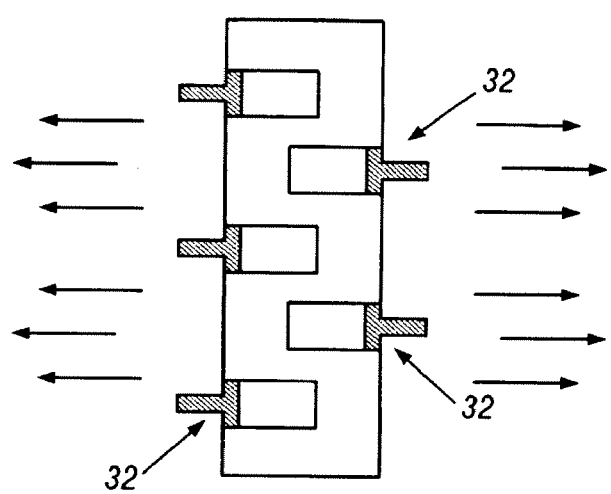
Figure 8C:
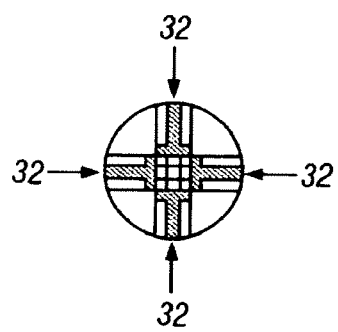
Figure 8D:
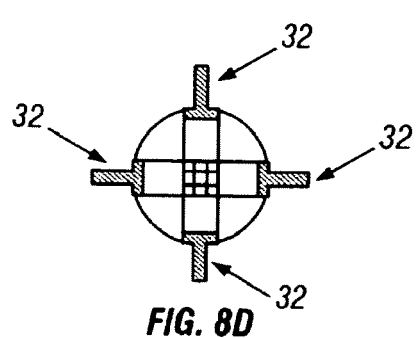

A piston type apparatus is shown in FIGS. 8A-8D and comprises a series of pistons 32 facing radially outwardly and used as a mechanism to expand the bistable expandable tubulars and connectors. When energized, the pistons 32 apply a radially directed force to deploy the bistable expandable tubular assembly as per the inflatable packer element. FIGS. 8A and 8C illustrate the pistons retracted while FIGS. 8B and 8D show the pistons extended. The piston type apparatus can be actuated hydraulically, mechanically or electrically.

A plug type actuator is illustrated in FIGS. 9A and 9B and comprises a plug 34 that is pushed or pulled through the bistable expandable tubulars 24 or connectors as shown in FIG. 9A. The plug is sized to expand the bistable cells past their critical point where they will snap to a final expanded diameter as shown in FIG. 9B.

Figure 10A:
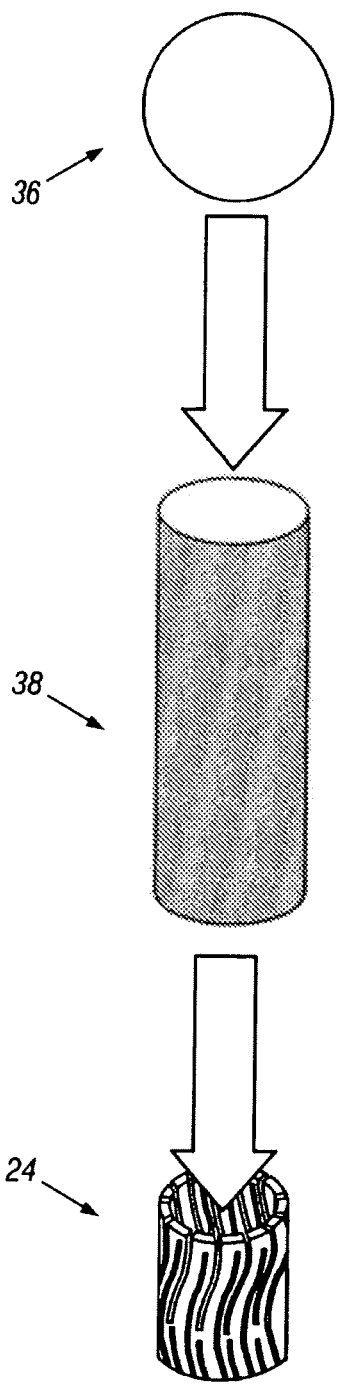
FIGS. 10A and 10B illustrate a ball type of deployment device.
Figure 10B:
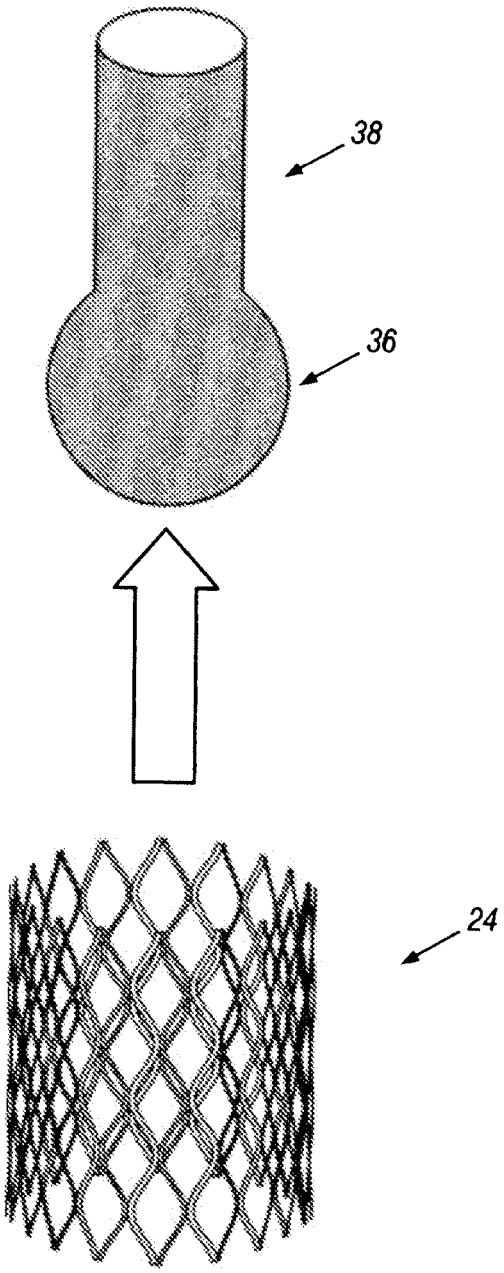

A ball type actuator is shown in FIGS. 10A and 10B and operates when an oversized ball 36 is pumped through the middle of the bistable expandable tubulars 24 and connectors. To prevent fluid losses through the cell slots, an expandable elastomer based liner 38 is run inside the bistable expandable tubular system. The liner 38 acts as a seal and allows the ball 36 to be hydraulically pumped through the bistable tubular 24 and connectors. The effect of pumping the ball 36 through the bistable expandable tubulars 24 and connectors is to expand the cell geometry beyond the critical bistable point, allowing full expansion to take place as shown in FIG. 10B. Once the bistable expandable tubulars and connectors are expanded, the elastomer sleeve 38 and ball 36 are withdrawn.

Radial roller type actuators also can be used to expand the bistable tubular sections. FIG. 12 illustrates a motor driven expandable radial roller tool. The tool comprises one or more sets of arms 58 that are expanded to a set diameter by means of a mechanism and pivot. On the end of each set of arms is a roller 60. Centralizers 62 can be attached to the tool to locate it correctly inside the wellbore and the bistable tubular 24. A motor 64 provides the force to rotate the whole assembly, thus turning the roller(s) circumferentially inside the wellbore. The axis of the roller(s) is such as to allow the roller(s) to rotate freely when brought into contact with the inner surface of the tubular. Each roller can be conically-shaped in section to increase the contact area of roller surface to the inner wall of the tubular. The rollers are initially retracted and the tool is run inside the collapsed bistable tubular. The tool is then rotated by the motor 64, and rollers 60 are moved outwardly to contact the inner surface of the bistable tubular. Once in contact with the tubular, the rollers are pivoted outwardly a greater distance to apply an outwardly radial force to the bistable tubular. The outward movement of the rollers can be accomplished via centrifugal force or an appropriate actuator mechanism coupled between the motor 64 and the rollers 60.

The final pivot position is adjusted to a point where the bistable tubular can be expanded to the final diameter. The tool is then longitudinally moved through the collapsed bistable tubular, while the motor continues to rotate the pivot arms and rollers. The rollers follow a shallow helical path 66 inside the bistable tubular, expanding the bistable cells in their path. Once the bistable tubular is deployed, the tool rotation is stopped and the roller retracted. The tool is then withdrawn from the bistable tubular by a conveyance device 68 that also can be used to insert the tool.

FIG. 13 illustrates a hydraulically driven radial roller deployment device. The tool comprises one or more rollers 60 that are brought into contact with the inner surface of the bistable tubular by means of a hydraulic piston 70. The outward radial force applied by the rollers can be increased to a point where the bistable tubular expands to its final diameter. Centralizers 62 can be attached to the tool to locate it correctly inside the wellbore and bistable tubular 24. The rollers 60 are initially retracted and the tool is run into the collapsed bistable tubular 24. The rollers 60 are then deployed and push against the inside wall of the bistable tubular 24 to expand a portion of the tubular to its final diameter. The entire tool is then pushed or pulled longitudinally through the bistable tubular 24 expanding the entire length of bistable cells 23. Once the bistable tubular 24 is deployed in its expanded state, the rollers 60 are retracted and the tool is withdrawn from the wellbore by the conveyance device 68 used to insert it. By altering the axis of the rollers 60, the tool can be rotated via a motor as it travels longitudinally through the bistable tubular 24.

Power to operate the deployment device can be drawn from one or a combination of sources such as: electrical power supplied either from the surface or stored in a battery arrangement along with the deployment device, hydraulic power provided by surface or downhole pumps, turbines or a fluid accumulator, and mechanical power supplied through an appropriate linkage actuated by movement applied at the surface or stored downhole such as in a spring mechanism.

The bistable expandable tubular system is designed so the internal diameter of the deployed tubular is expanded to maintain a maximum cross-sectional area along the expandable tubular. This feature enables mono-bore wells to be constructed and facilitates elimination of problems associated with traditional wellbore casing systems where the casing outside diameter must be stepped down many times, restricting access, in long wellbores.

The bistable expandable tubular system can be applied in numerous applications such as an expandable open hole liner where the bistable expandable tubular 24 is used to support an open hole formation by exerting an external radial force on the wellbore surface. As bistable tubular 24 is radially expanded, the tubular moves into contact with the surface forming wellbore 29. These radial forces help stabilize the formations and allow the drilling of wells with fewer conventional casing strings. The open hole liner also can comprise a material, e.g. a wrapping, that reduces the rate of fluid loss from the wellbore into the formations. The wrapping can be made from a variety of materials including expandable metallic and/or elastomeric materials. By reducing fluid loss into the formations, the expense of drilling fluids can be reduced and the risk of losing circulation and/or borehole collapse can be minimized.

Liners also can be used within wellbore tubulars for purposes such as corrosion protection. One example of a corrosive environment is the environment that results when carbon dioxide is used to enhance oil recovery from a producing formation. Carbon dioxide ($CO_2$) readily reacts with any water ($H_2O$) that is present to form carbonic acid ($H_2CO_3$). Other acids can also be generated, especially if sulfur compounds are present. Tubulars used to inject the carbon dioxide as well as those used in producing wells are subject to greatly elevated corrosion rates. The present invention can be used to place protective liners, e.g. a bistable tubular 24, within an existing tubular to minimize the corrosive effects and to extend the useful life of the wellbore tubulars.

Another exemplary application involves use of the bistable tubular 24 as an expandable perforated liner. The open bistable cells in the bistable expandable tubular allow unrestricted flow from the formation while providing a structure to stabilize the borehole.

Still another application of the bistable tubular 24 is as an expandable sand screen where the bistable cells are sized to act as a sand control screen. Also, a filter material can be combined with the bistable tubular as explained below. For example, an expandable screen element can be affixed to the bistable expandable tubular. The expandable screen element can be formed as a wrapping around bistable tubular 24. It has been found that the imposition of hoop stress forces onto the wall of a borehole will in itself help stabilize the formation and reduce or eliminate the influx of sand from the producing zones, even if no additional screen element is used.

The above described bistable expandable tubulars can be made in a variety of manners such as: cutting appropriately shaped paths through the wall of a tubular pipe thereby creating an expandable bistable device in its collapsed state; cutting patterns into a tubular pipe thereby creating an expandable bistable device in its expanded state and then compressing the device into its collapsed state; cutting appropriate paths through a sheet of material, rolling the material into a tubular shape and joining the ends to form an expandable bistable device in its collapsed state; or cutting patterns into a sheet of material, rolling the material into a tubular shape, joining the adjoining ends to form an expandable bistable device in its expanded state and then compressing the device into its collapsed state.

The materials of construction for the bistable expandable tubulars can include those typically used within the oil and gas industry such as carbon steel. They can also be made of specialty alloys (such as a monel, inconel, hastelloy or tungsten-based alloys) if the application requires.

The configurations shown for the bistable tubular 24 are illustrative of the operation of a basic bistable cell. Other configurations may be suitable, but the concept presented is also valid for these other geometries.

Figure 14:
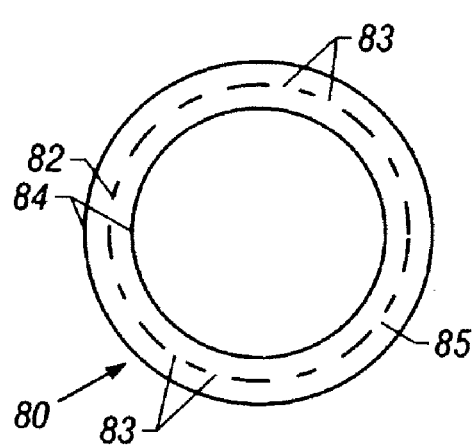
FIG. 14 is a cross sectional view of one embodiment of the packer of the present invention.
Figure 15:
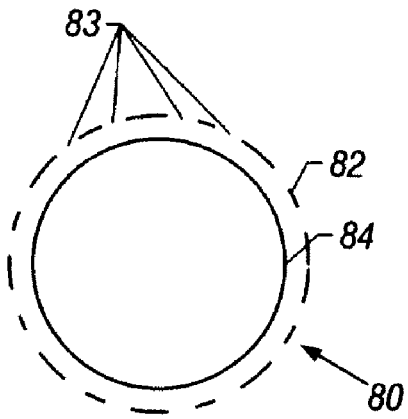
FIG. 15 is a cross sectional view of another embodiment of the packer of the present invention.

In FIGS. 14 and 15, a packer 80 formed of bistable cells is illustrated. The packer 80 has a tubular 82 formed of bistable cells 83, such as those previously discussed. In addition, the packer 80 has at least one seal 84 along at least a portion of its length. An exemplary seal 84 may include one or more layers positioned internally, externally, or both with respect to tubular 82. Additionally, the layer(s) may be intermixed with the openings formed in the cells.

FIG. 14 illustrates an embodiment having an internal and an external seal 84. FIG. 15 illustrates a packer 80 having only an internal seal 84. The seal 84 may be formed of an elastomer or other material. Further, the properties of the seal 84 allow it to at least match the expansion ratio of the tubular 82. Folds or other design characteristics of the seal 84 may be used to facilitate the expansion.

Also, a resin or catalyst 85 may be used to allow the seal 84 to harden after setting. In one alternative embodiment a resin or other flowable material is placed between the layers of seals 84 (as in FIG. 14). Once the packer 80 is placed in the well and expanded, the flowable material may be hardened or otherwise altered to improve the sealing characteristics of the packer 80. In some applications, hardening of the resin or other material requires heating of the material by a service tool. The packer 80 can be expanded as described herein, and may comprise a variety of bistable cells. In one embodiment of use, the packer 80 is deployed on a run-in tool that includes an expanding tool. The packer 80 is positioned at the desired location and expanded to seal against the walls of the casing or other tubular. Typically, the packer 80 is connected to a tubing or other conduit that extends downhole below the packer 80. The packer 80 provides a seal in the annulus to prevent or restrict fluid flow longitudinally in the well (the typical use for packers). The present invention also may act as a well anchor which includes or excludes the seal 84.

Figure 16:
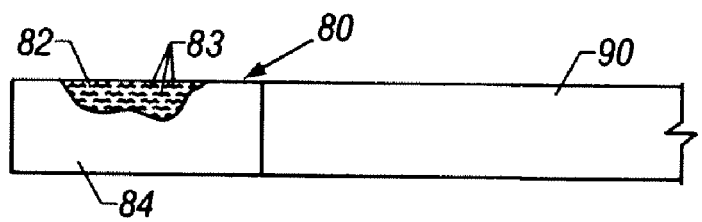
FIG. 16 is a side elevation view of an embodiment of the present invention in a contracted state.
Figure 17:
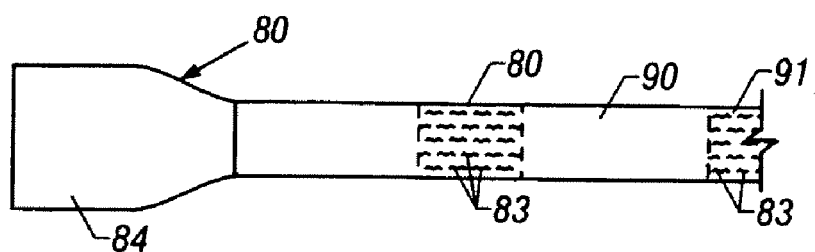
FIG. 17 is a side elevation view of an embodiment of the present invention in an expanded state.

In FIG. 16, an alternative embodiment is illustrated in which the packer 80 forms a portion of a conduit. In the embodiment shown, a well conduit 90 (such as a tubing) has a portion (marked as the packer 80) that is cut to form the bistable cells. The packer portion 80 has a seal 84 thereon as previously described. In FIG. 16, a portion of the seal material 84 is illustrated as removed to reveal the bistable cells 83 in the underlying tubular 82. In FIG. 17, the packer portion 80 is illustrated in its expanded state. It should be noted that in typical applications the well conduit 90 which does not have bistable cells formed therein, does not expand. Thus, one embodiment for attaching the well conduit to the packer 80 is to form the packer 80 as an integral part of the well conduit 90 (note that a welded connection resembles this embodiment and is an alternative method of forming the present invention). Other methods include conventional methods of non-integral connection.

In alternative embodiments, the well conduit has a plurality of bistable cell packers 80 formed thereon. In yet another alternative embodiment, a portion or portions 91 of the well conduit in addition to the packer portions 80 are formed of bistable cells so that these other portions also undergo expansion (see FIG. 17). The other portions may or may not have a material applied thereto. For example, the other portion may have a screen or filter material applied thereto to provide a well sand screen.

Figure 18A:
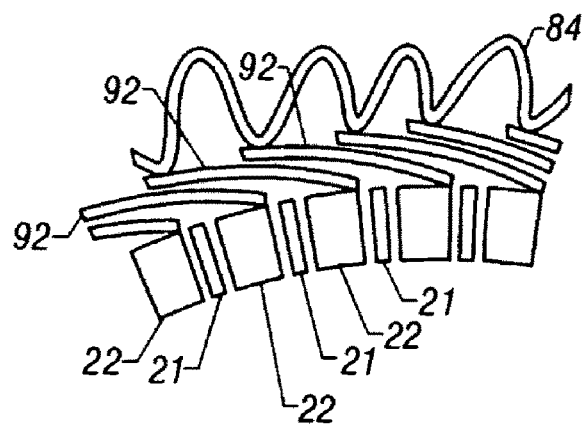
FIGS. 18 A-C are schematic views of an alternative embodiment of the present invention.
Figure 18B:
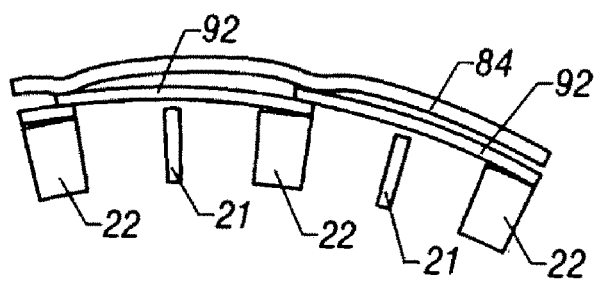
Figure 18C:
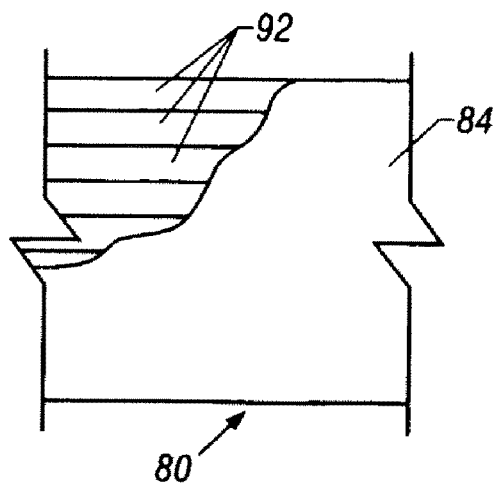

Referring to FIGS. 18 A-C, an alternative design of the present invention is illustrated in a schematic, partial cross-sectional view. The expandable packer is shown in the retracted and expanded states, respectively, and in partial side elevational view (FIG. 18C). The packer shown includes a base tubular 82 formed of thin struts 21 and thick struts 22 forming bistable cells 23/83 as previously described. Slats 92 are attached to the tubing 82 at one edge and extend generally longitudinally in the embodiment shown (see FIG. 18C). Specifically, each slat 92 is attached to the tubing 82 at the thick struts 22, and the width of the slats is such that they overlap at least the adjacent slat when the tubing 82 is in the expanded state. Although illustrated as having a slat attached to each of the thick struts, the packer may have a slat attached to alternate thick struts 22 or in other configurations. Furthermore, the slats may extend in a direction other than the longitudinal direction. The slats 92 slide over one another during expansion so that the outside of the tubing 82 is covered by the overlapping slats 92.

A seal 84 may be attached to the slats 92 to provide the seal for the packer. Although shown in the figures as folded, the seal 84, may have other characteristics that facilitate its ability to expand with the slats 92 and tubular 82. Also, the seal 84 may have other characteristics previously mentioned (e.g., resin, internal seal, etc.).

It should be noted that although described as a packer, the present invention may be used to provide isolation over a long length as opposed to a traditional packer or downhole tool which generally seals only a relatively short longitudinal distance. Thus, the present invention may be used in a manner similar to a casing to provide isolation for an extended length.

Figure 19:
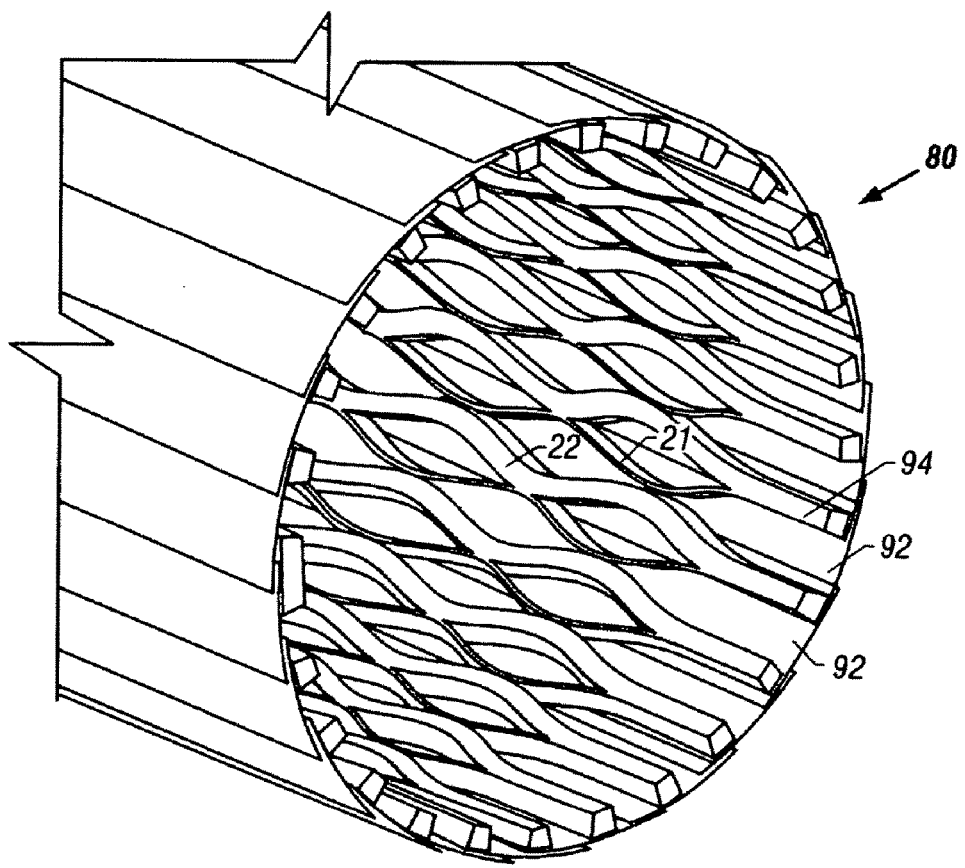
FIG. 19 is a perspective view of an alternative embodiment of the present invention.

In FIG. 19, a perspective view of packer 80 (or isolation device) having a plurality of slats 92 attached thereto is illustrated in an overlapping arrangement as previously described. The tubing 82 includes end extensions 94 that extend longitudinally from the endmost cells. The slats 92 may be attached to the end extensions 94, to certain portions of the thick struts 22 and/or to certain thick struts 22. In one embodiment, for example, the struts 92 are attached to the thick struts which are longitudinally aligned with the end extensions 94. Although generally shown as attached at an edge of the slats 92, the slats also may attach to the tubing 82 at a position intermediate the edges.

Figure 20:
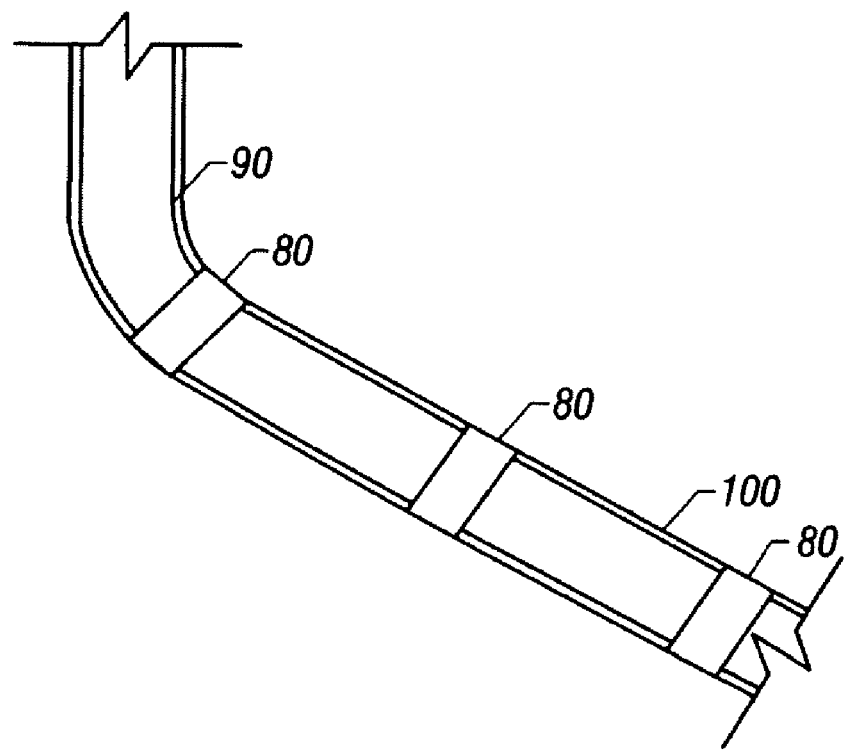
FIG. 20 is a schematic view of an alternative embodiment of the present invention.

In FIG. 20, an expandable tubing (or conduit) 90 is illustrated positioned in a well 100. The conduit 90 includes a plurality of spaced packers 80 or expandable sealing devices. The expandable packers 80 engage the wellbore wall preventing annular flow thereby. Therefore, any microannulus formed between the expandable tubing 90 and the well 100 (which may include a casing) is sealed in the longitudinal direction to restrict or prevent unwanted flow thereby. The conduit 90 may include one or more such packers 80, as desired, to control the flow. Further, the packers 80 may be spaced at regular intervals or at some other predetermined spacing to control the flow in the annulus as needed.

Figure 21:
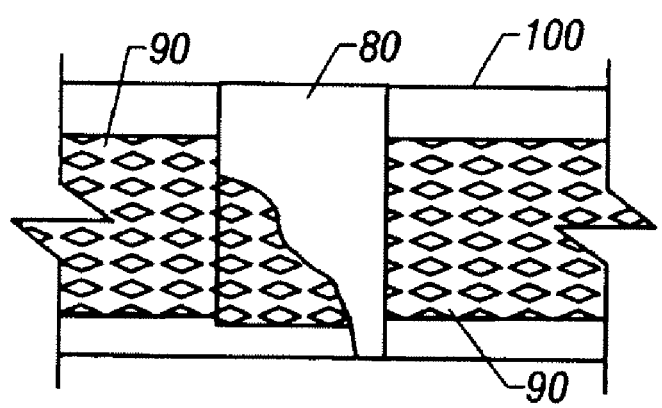
FIG. 21 is a schematic view of an alternative embodiment of the present invention.

In one example, illustrated schematically in FIG. 21, the individual joints of tubing 90 are interconnected by a packer 80 to compartmentalize each joint of conduit from the adjacent joint(s). The packer 80 can be a separate connector as shown in FIG. 21 or it can be formed as part of the joint. Accordingly, the packer 80 can be positioned at an end of the joint 90, in the middle of the joint 90, or at any other location along its length. In one embodiment both conduit 90 and packers 80, of FIGS. 20 and 21, are formed of bistable cells.

Referring generally to FIGS. 22 A-B, an alternative embodiment of the present invention is disclosed. The device shown in these figures may be used as a packer, hanger, casing patch, or other device requiring expansion and is generally referred to herein in reference to these figures as an expandable tubular 120 for ease of description. The expandable tubular 120 comprises a series of cells 122 formed therein, such as by laser cutting, jet cutting, water jet cutting or other manufacturing methods. The cells 122 are oriented such that a number of longitudinal struts 24 are formed on the expandable tubular 120. Thus, as shown in the figures, the longitudinal struts 124 lie between longitudinal lengths of cells 122 with the cells 122 having relatively thinner struts 126 extending between adjacent longitudinal struts 124. As shown in the figures, as the adjacent longitudinal struts 124 are moved longitudinally relative to one another (e.g. in opposite directions), the cells 122 open to expand the structure radially. Not all of the longitudinal struts 124 must move; alternate longitudinal struts 124 may be moved while the other struts remain stationary. The relative movement of the longitudinal struts 124 provides the expansion of the cells 122 and the expandable tubular 120. This type of cell is an example of an expandable cell that is not bistable.

A locking mechanism 128 may be used to maintain the expanded position of the expandable tubular 120. As shown in FIGS. 22 A-B, the expandable tubular may comprise one or more locking mechanisms 128 spaced along the length of the expandable tubular 120 and spaced radially about the expandable tubular 120. One embodiment of the locking mechanism is shown in FIGS. 23 A-B. In the embodiment shown, the locking mechanism 128 comprises a detent (or finger) 130 extending from one longitudinal strut 124 and cooperating with a set of ratchet teeth 132 provided on another longitudinal strut 124. The ratchet teeth 132 extend from a ramp area 134 of the longitudinal strut 124 to accommodate for the relative movement of the detent 130 to the longitudinal strut 124 having the ratchet teeth 132. The ratchet teeth 132 generally allow movement of the detent 130 thereon in a first direction associated with the expansion of the expandable tubular 120, and prevent movement of the detent 130 in the opposite direction. Once in the expanded position, the detent 130 acts as a locked strut preventing retraction of the expandable tubular 120. To increase the structural integrity of the expanded tubular 120 and to resist forces tending to move the expandable tubular 120 from an expanded state or position to a reduced position, the expandable tubular 120 may include a plurality of locking mechanisms 128.

Although shown as a ratchet, as an alternative the locking mechanism may have fewer discrete positions, such as one, in which the detent locks in the fully expanded position only. In another embodiment the detent may comprise a resilient finger biased toward an extended position that snaps into a groove in an adjacent longitudinal strut 124. Likewise, the adjacent struts 124 may each have resilient detents that cooperate to lock the device in the expanded position only upon the tubular 120 achieving the expanded position. These are only a few examples of the many possible alternatives for the locking mechanism 128.

Also, various other tubular expansion mechanisms and expandable cells may be utilized, such as expandable tubulars and other devices. For example, details of one type of expandable cell are illustrated in FIGS. 24A, 24B, 25A and 25B. In this embodiment, as in other embodiments, the cell is transitioned from a compressed state to an expanded state.

During movement from the compressed state to the expanded state and depending upon the environmental conditions as well as the materials used, material thickness and other design parameters of the cell and devices formed from the cell, some areas of the cell and struts may experience plastic deformation. In FIGS. 24A, 24B, 25A and 25B alternative embodiments of a cell are illustrated in compressed and expanded states. In these embodiments, one of the struts 21 (shown as the thinner, upper strut) has thinned portions 140 that serve as flexible hinges or joints. The thinned portions 140 are preferably placed at areas where plastic deformation of the strut is likely to occur as the strut moves from a compressed to an expanded state. Thus, for example, the thinned portions 140 may be placed near the intersection of the struts 21, 22 to provide an area that is less susceptible to plastic deformation. Although the figures show a plurality of thinned portions 140, the strut may include a single thinned portion 140, for example, at an area of increased plastic deformation. Also, the thinned portions 140 may be placed in other positions along the struts 21, 22 for other purposes. The thinned areas 140 define linkages 142 there between that comprise portions which are generally thicker than the thinned portions 140. Placing a plurality of thinned portions 140 along the length of a strut 21, 22 produces a plurality of linkages 142.

Another factor in determining the positioning of the thinned portions 140 is the number, placement, and design of the linkages. Although shown in the figures as having a uniform thickness, the linkages 142 may also have a variation in thickness to further tailor the expansion, contraction, and other characteristics of the cell as desired. Therefore, in one broad aspect of the inventions, at least one of the struts 21, 22 has a thickness that varies. Also, other factors may be considered in placement of the thinned portions 140 and the thickness variations of the struts 21, 22. Also, the thinned portions may occur at the intersection of the struts 21, 22.

Figure 24A:
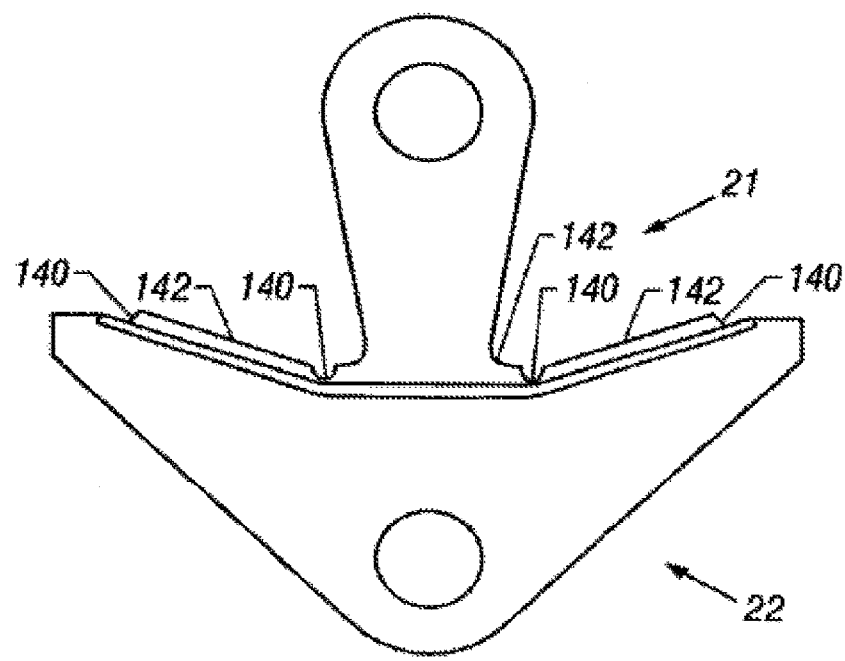
FIGS. 24 A-B are side elevational views of an alternate embodiment of an expandable cell in its contracted and expanded positions, respectively.
Figure 24B:
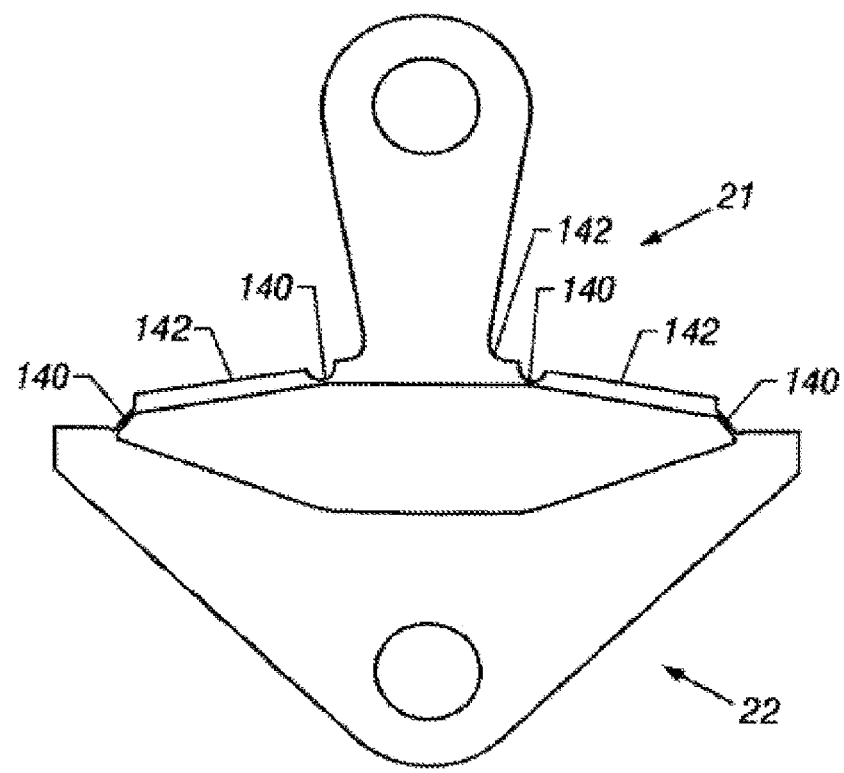
Figure 25A:
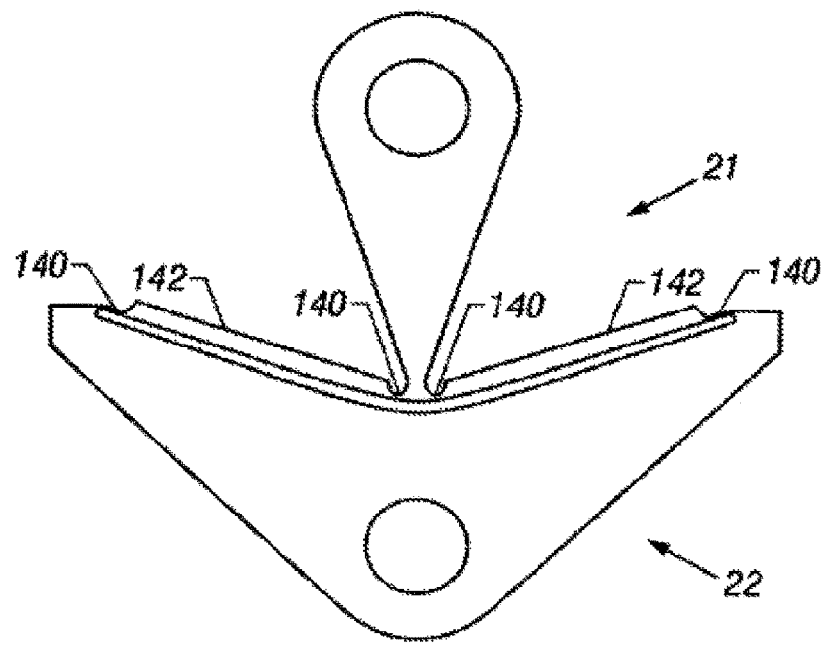
FIGS. 25 A-B are side elevational views of a cell similar to that illustrated in FIGS. 24 A-B deployed in its contracted and expanded positions, respectively.
Figure 25B:
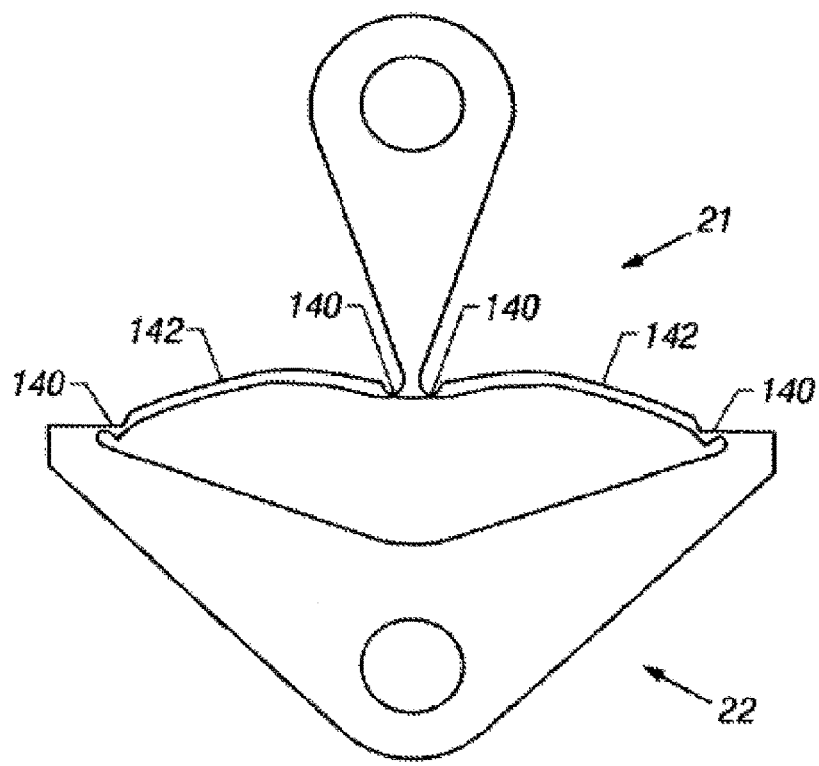

In FIGS. 24A and 24B a cell with three linkages 142 is illustrated; and in FIGS. 25A and 25B a cell with two linkages is illustrated. Although FIGS. 24A-25B disclose only a single cell, the cells may be incorporated into a tool, such as a tube, having a plurality of cells such as that shown in FIGS. 4A and 4B. The figures illustrate a single cell to more clearly show the basic concept and the cell design. The handles shown in the figures are not a part of the cell structure, but are merely used on test cells to facilitate testing of the cells.

Figure 26A:
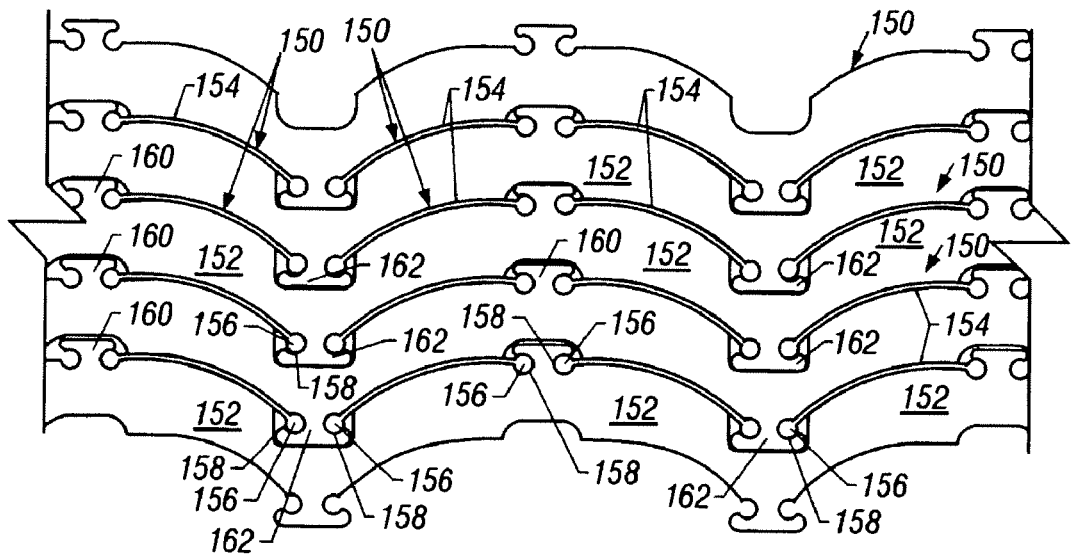
FIGS. 26 A-B illustrate another embodiment of expandable cells displayed in their contracted and expanded positions, respectively.
Figure 26B:
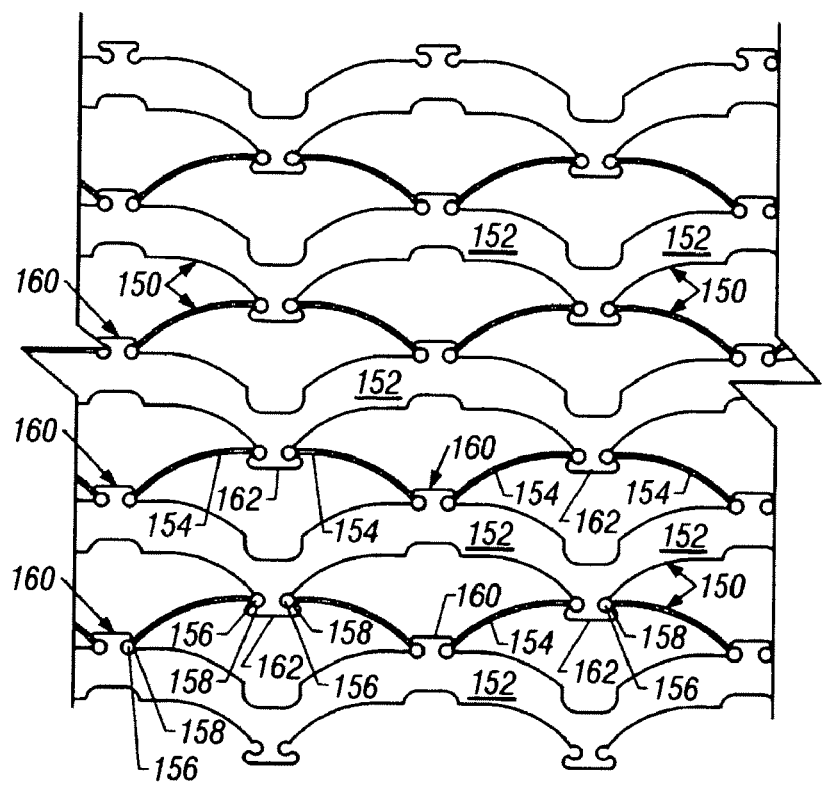

Referring generally to FIGS. 26A and 26B, another embodiment of expandable cells, labeled as expandable cells 150, is illustrated. Each expandable cell 150 comprises a thick strut 152 and one or more thin struts 154, e.g. two thin struts 154. In the embodiment illustrated, each expandable cell 150 comprises a pair of thin struts, and each thin strut 154 has a pair of ends 156 pivotably coupled to adjacent thick struts, respectively. Ends 156 may comprise pins that are pivotably received in corresponding sockets 158.

As the plurality of expandable cells 150 is moved from the contracted state illustrated in FIG. 26A to the expanded state illustrated in FIG. 26B, thin struts 154 deform sufficiently to permit pivoting of pins 156 in their corresponding sockets 158. As illustrated best in FIG. 26B, the pairs of thin struts 154 that form each cell 150 have outlying ends 156 pivotably coupled to upper attachment regions 160 of the lower thick strut 152. The opposite ends of each pair of thin struts 154 are pivotably coupled to a lower attachment region 162 of the next upwardly adjacent thick strut 152. It should be noted that positional terms such as upper and lower are merely used to facilitate explanation of the location of various features relative to the figures provided and should not be construed as limiting.

Figure 27A:
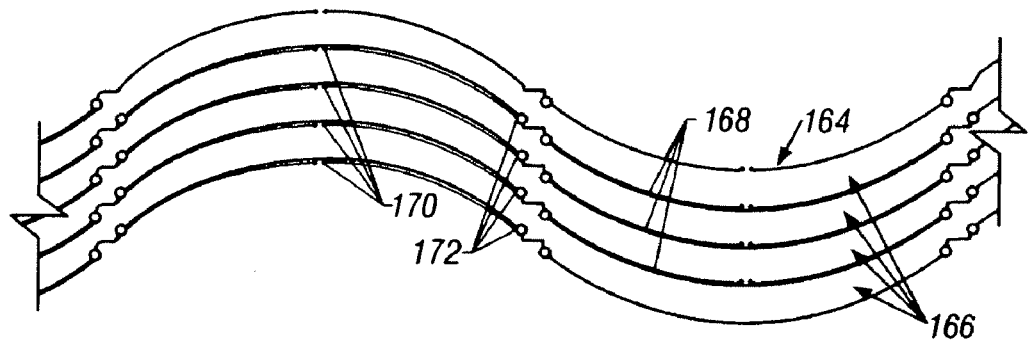
FIGS. 27 A-B illustrate another embodiment of expandable cells displayed in their contracted and expanded positions, respectively.
Figure 27B:
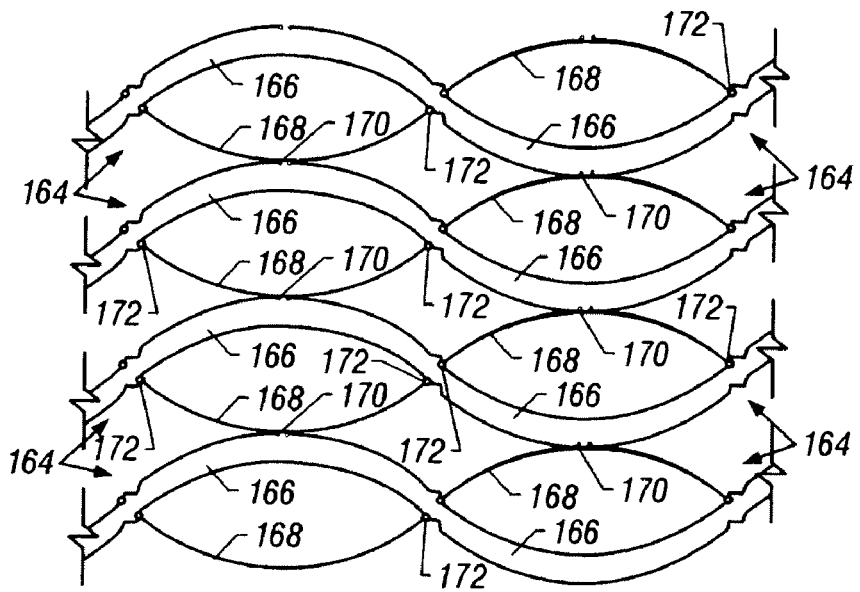

In another embodiment illustrated in FIGS. 27A and 27B, a plurality of expandable cells, labeled with reference numeral 164, each comprise a thick strut 166 and one or more thin struts 168. Each thick strut 166 is generally arcuate and connected to a corresponding thin strut 168 at a fixed connection region 170 disposed at a generally central location along the outer or convex portion of the arcuate thick strut. The outer ends of each thin strut 168 are pivotably coupled to the next adjacent thick strut 166 via a pivot connection 172 that may comprise a ball and socket.

As the plurality of cells are moved from the contracted state illustrated in FIG. 27A to the expanded state illustrated in FIG. 27B, thin struts 168 flex or deform as their outer ends pivot at each pivot connection 172. As with many of the other cells described herein, when the thin struts 168 move past their point of greatest flexure, the stored spring energy tends to force the cells 164 to their stable expanded state illustrated in FIG. 27B. Thus, as with the bistable cells illustrated in FIGS. 26A and 26B, cells 164 move between a stable contracted state and a stable expanded state.

Figure 28A:
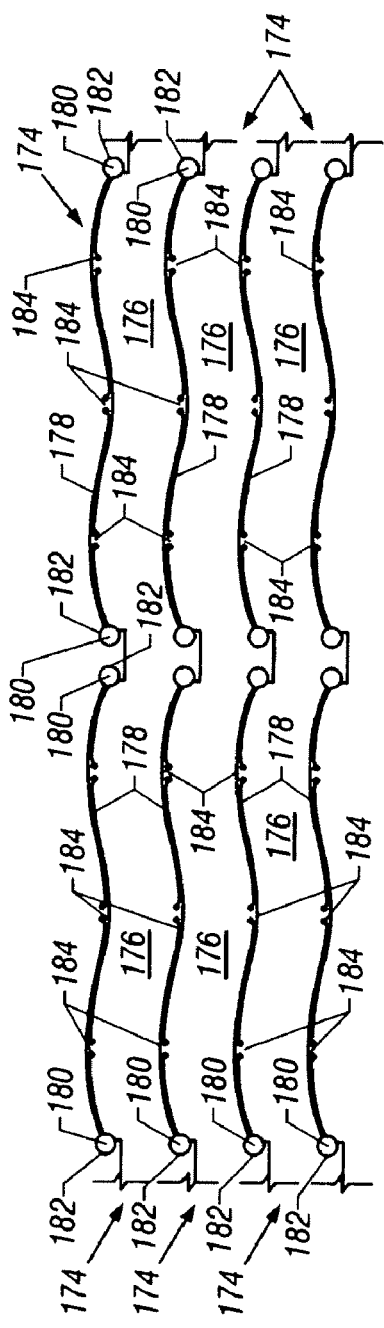
FIGS. 28 A-B illustrate another embodiment of expandable cells displayed in their contracted and expanded positions, respectively.
Figure 28B:
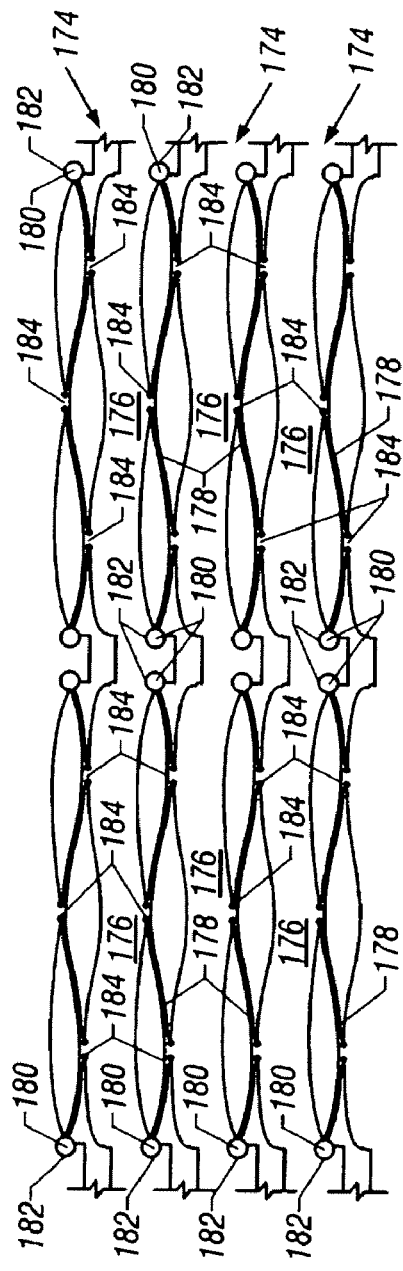

Another expandable cell embodiment is illustrated in FIGS. 28A and 28B. In this embodiment, each expandable cell 174 is formed of a thick strut 176 and a thin strut 178. Each thin strut 178 has a pair of ends 180 that are pivotably coupled to a thick strut. For example, a given thick strut may comprise a pair of sockets 182 to pivotably receive pin or ball shaped ends 180. Additionally, thin strut 178 is fixedly coupled to adjacent thick struts 176 in an alternating pattern. For example, each cell in the illustrated embodiment comprises three fixed couplings 184 that alternate between adjacent thick struts 176. With this design, the expandable cells 174 again are movable between a stable contracted state as illustrated in FIG. 28A and a stable expanded state as illustrated in FIG. 28B.

With reference to FIGS. 29A and 29B, another expandable cell design is illustrated. In this embodiment, each of a plurality of expandable cells 186 comprises a thick strut 188 and at least a pair of stacked thin struts 190, 192, respectively. Thin struts 190, 192 are generally disposed in a stacked orientation and connected by a linking member 194. Thin strut 192 comprises a pair of ends 196 affixed to a corresponding thick strut 188. An intermediate connection region 198 of thin strut 192 is affixed to the next adjacent thick strut 188, as best illustrated in FIG. 29B. Thin strut 190, on the other hand, has unattached ends 200. Ends 200 are captured in an abutting engagement with a notched region 202 formed in the same thick strut 188 to which ends 196 are affixed. As the plurality of expandable cells 186 are moved from the contracted state illustrated in FIG. 29A to the expanded state illustrated in FIG. 29B, each pair of thin struts 190 and 192 deforms to a deflection point where stored energy in the thin struts is maximized. As the thin struts are moved past this deflection point, the stored energy is released to facilitate expansion of the cells to their expanded state.

Of course, with any of these types of bistable cells, the degree of expansion may be limited by an external barrier. For example, if the bistable cells are used to form a tubular, the tubular may be expanded against a wellbore wall that prevents the cells from moving to their fully expanded condition. Typically, the size of the tubular is selected to permit expansion of the cells at least past the point of maximum deformation. Thus, depending on the material used, the cells may actually cooperate to apply an outwardly directed radial force against the wellbore wall.

Figure 30A:
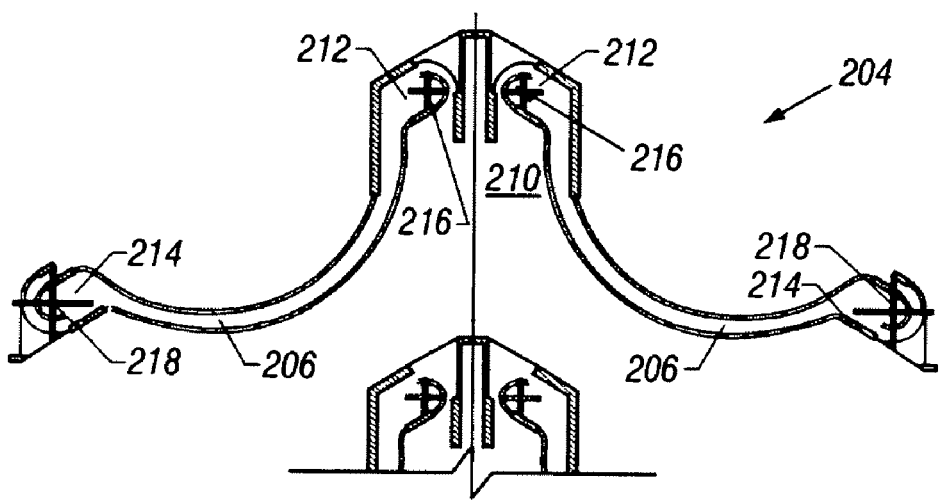
FIGS. 30 A-B illustrate another embodiment of an expandable cell displayed in its contracted and expanded position, respectively.
Figure 30B:
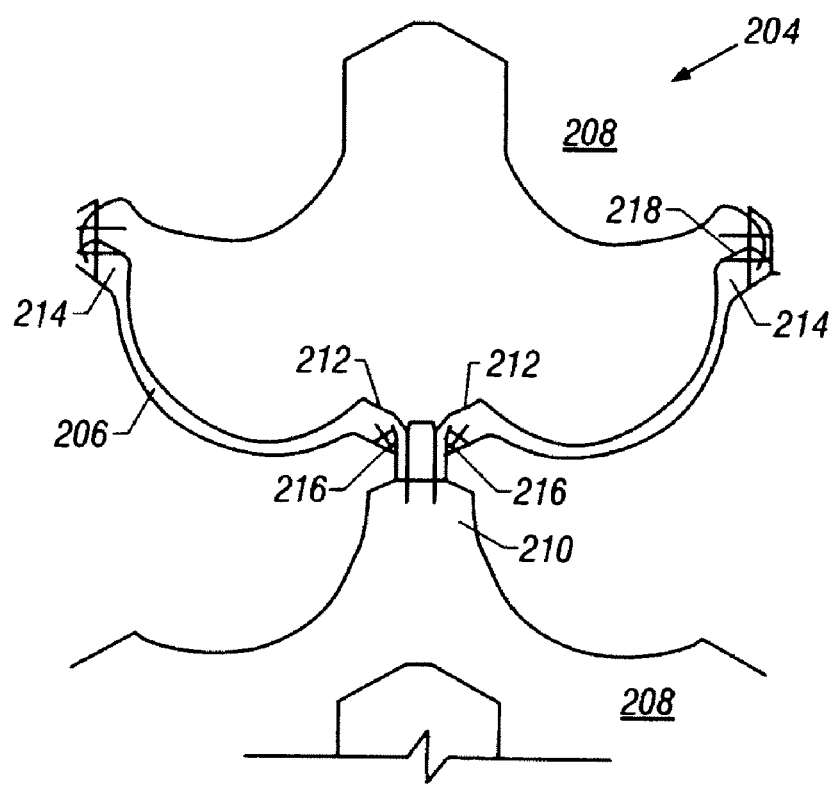

Referring generally to FIGS. 30A and 30B, another expandable cell design is illustrated. Each expandable cell 204 comprises a pair of arcuate thin struts 206 pivotably coupled to a corresponding thick strut 208 at a generally centralized extended region 210 via pivot ends 212. Generally opposite pivot ends 212, thin struts 206 comprise outer pivot ends 214 that are pivotably coupled to the next adjacent thick strut 208. Pivot ends 212 and 214 can be formed in a variety of configurations, such as ball joints, pin joints, etc. Removal of each thin strut 206 is prevented by appropriate ligaments 216 and 218 disposed at pivot ends 212 and 214, respectively. The ligaments 216 and 218 are coupled between the thin strut 206 and the corresponding thick struts 208.

Figure 31A:
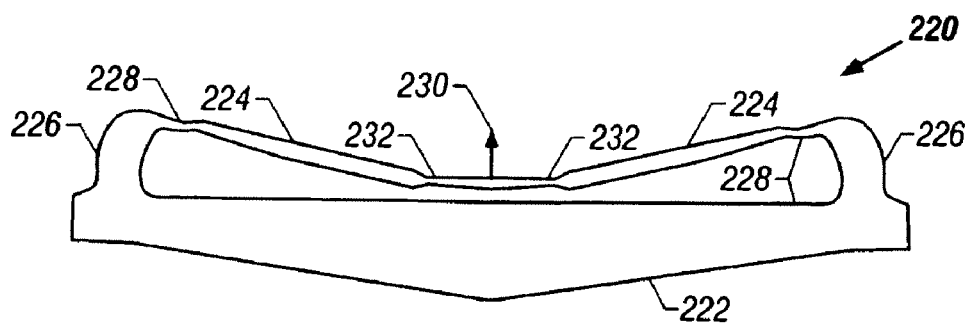
FIGS. 31 A-C illustrate a cell with energy storage members moving from a contracted state to an expanded state.
Figure 31B:
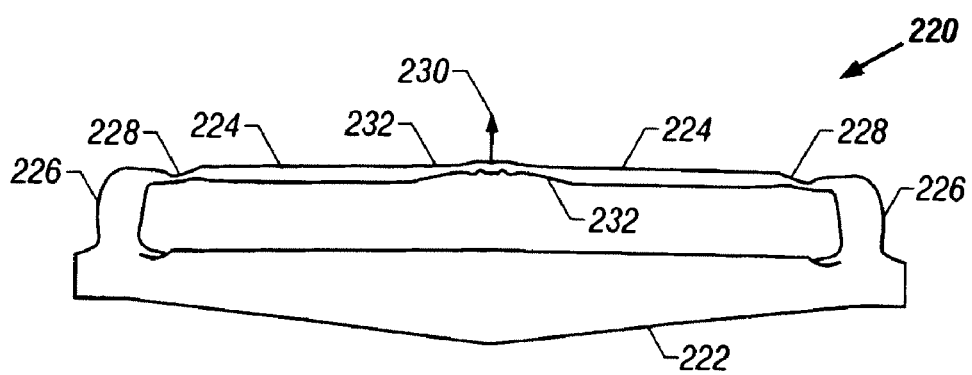
Figure 31C:
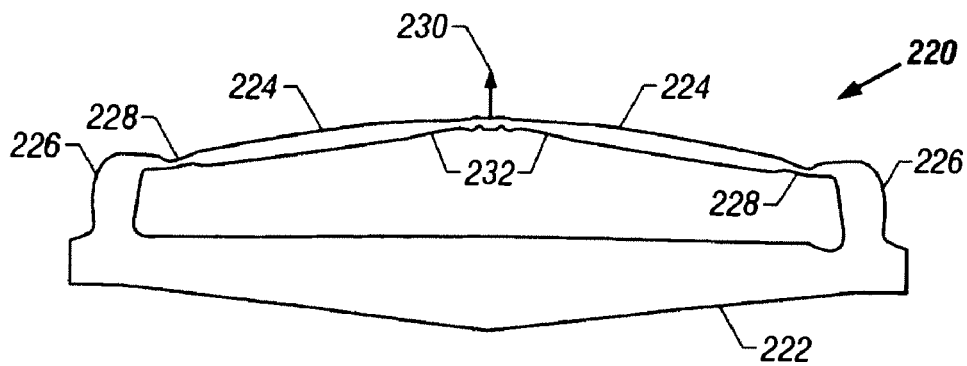

In FIGS. 31A-31C, a different type of expandable cell 220 is illustrated. In this embodiment, a thick strut 222 is coupled to one or more thin struts 224 by one or more spring elements 226. In the particular embodiment illustrated, two spring elements 226 are formed generally in the shape of a horn, with the base of each horn connected to thick strut 222 and the tip of each horn coupled to the adjacent thin strut 224. In this embodiment, a thin strut 224 is connected to each spring element 226 by a flexible hinge 228. The two thin struts 224 are coupled to each other through a center beam 230 and a pair of flexible hinges 232.

As cells 220 are expanded from a contracted state, illustrated in FIG. 31A, to an expanded state, illustrated in FIG. 31 C, spring elements 226 flex outwardly and store spring energy. With this design, thin struts 224 typically do not undergo substantial deformation during movement from the contracted state to the expanded state. Rather, spring elements 226 are elastically deformed as they are forced outwardly during movement of center beam 230 from the contracted state to the expanded state. When spring elements 226 are flexed outwardly, they store spring energy at least to the point of maximum flexure illustrated in FIG. 31B where thin struts 224 are generally parallel with thick strut 222. Once center beam 230 moves past this point of maximum stored spring energy, spring elements 226 tend to release the stored energy and move inwardly, thereby forcing thin struts 224 and center beam 230 to the expanded position illustrated best in FIG. 31C. Deformation of hinges 228 and 232 facilitates the pivoting of thin struts 224 from the contracted state to the expanded state.

Figure 32A:
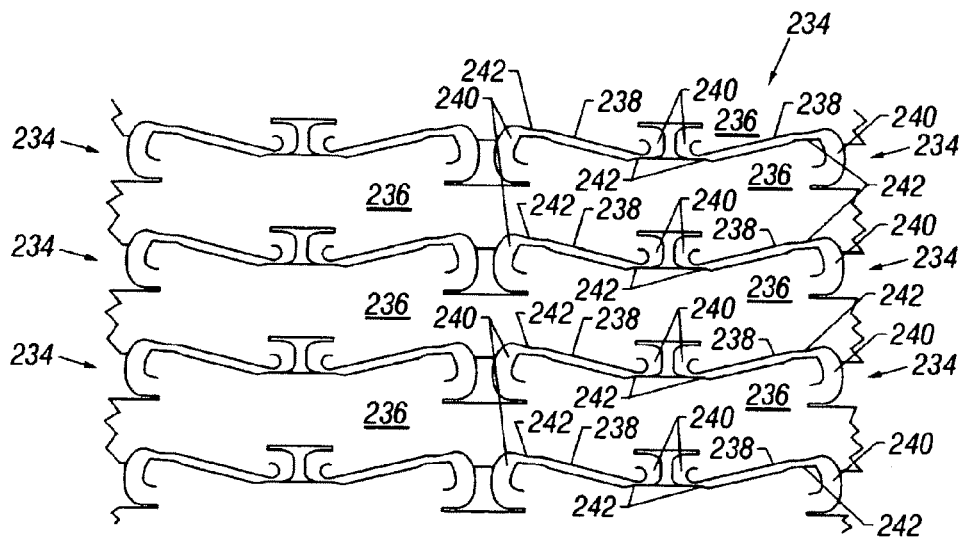
FIGS. 32A-32B illustrate another embodiment of the cell illustrated in FIGS. 31 A-C in a contracted position and expanded position, respectively.
Figure 32B:
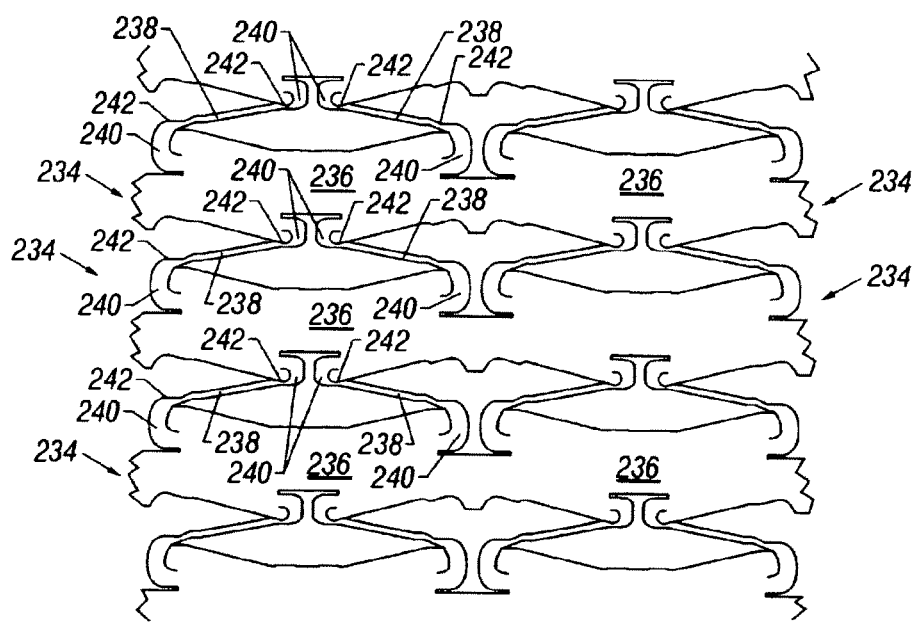

A double horn cell design is illustrated in FIGS. 32A and 32B. In this design, a plurality of thick struts 236 are coupled together via thin struts 238 and horn spring members 240. Specifically, each thin strut 238 is coupled to two horn spring members 240 to permit storage of a greater amount of energy. This greater energy storage provides added positive energy for opening cells 234 to their expanded positions as illustrated in FIG. 32B.

In the example illustrated, each double horn cell 234 has two outer horn spring members 240, coupled to one thick strut 236, and two inner horn spring members 240, coupled to the next adjacent thick strut 236. One thin strut 238 is coupled to each cooperating pair of inner and outer horn spring members via appropriate hinge regions 242. Thus, as the double horn cells 234 are moved from the contracted state illustrated in FIG. 32A to the expanded state illustrated in FIG. 32B, cooperating pairs of inner and outer horn spring members 240 are flexed outwardly to a point at which the thin struts 238 are generally aligned. Subsequent to this point of expansion, the horn spring members 240 begin to release the stored spring energy and force thin struts 238 towards the fully expanded state.

Figure 33:
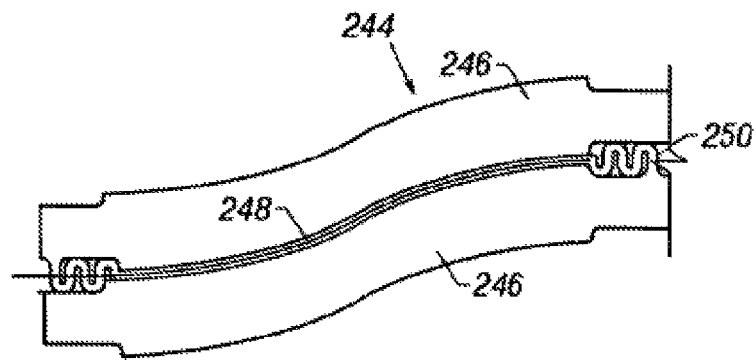
FIG. 33 illustrates another exemplary expandable cell design.

Other forms of spring elements also may be utilized in facilitating expansion of a variety of cell types. For example, in FIG. 33 an expandable cell 244 is illustrated in which adjacent thick struts 246 are coupled to a thin strut 248 by a different type of spring members 250. Spring members 250 may be coiled, undulating or arranged along other paths that accommodate the transitioning of thin strut 248 from the contracted state illustrated in FIG. 33 to an expanded state.

Figure 34:
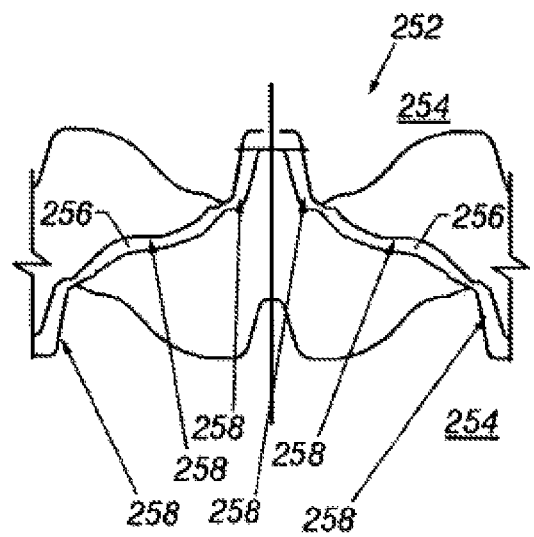
FIG. 34 illustrates another exemplary expandable cell design.

Another type of spring system is illustrated in FIG. 34 as an expandable cell 252. A pair of thick struts 254 are coupled by a pair of undulating thin struts 256. The design of thin struts 256 incorporates a plurality of spring elements 258 that both accommodate flexure of the thin struts 256 and expansion of the cell 252 by storing and then releasing spring energy. The spring energy is released as the thin struts transition past a point of maximum flexure towards the fully expanded state.

Figure 35A:
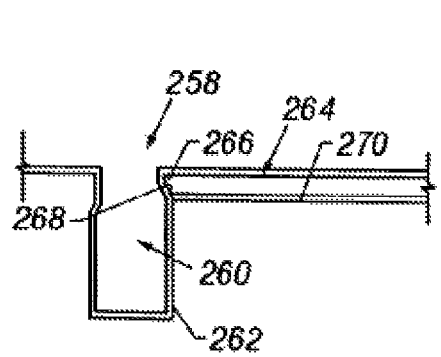
FIGS. 35 A-D illustrate an exemplary locking mechanism moving through various stages from a closed position to an open, locked position.
Figure 35B:
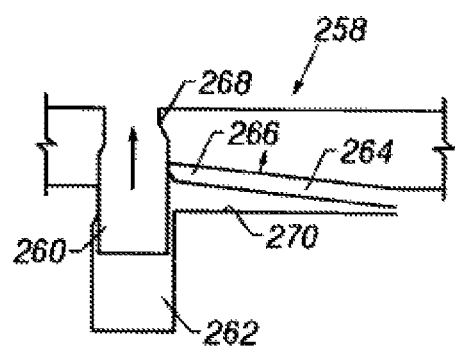
Figure 35C:
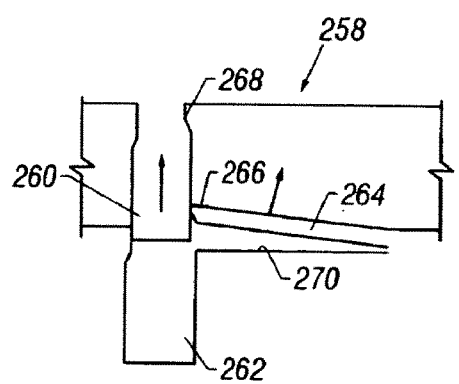

To secure the overall device, e.g. tubular, in the expanded position, a locking mechanism may be utilized to prevent the individual cells from contracting. Exemplary locking mechanisms may be associated with individual cells, or they may be located at one or more positions along the expandable device. In FIGS. 35A-35D, one type of locking mechanism 258 is illustrated. In this embodiment, a post 260 is slidably received in a corresponding recess 262. A ratchet finger 264 extends generally transversely towards post 260. Specifically, ratchet finger 264 comprises an engagement end 266 that resides in a recessed area 268 of post 260 when the overall device and locking mechanism 258 are in a contracted state, as illustrated in FIG. 35A.

Figure 35D:
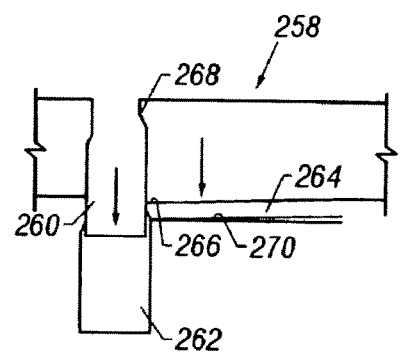

As the device, e.g. tubular, is expanded, ratchet finger 264 is flexed away from an adjacent support surface 270, as illustrated best in FIG. 35D. The ratchet finger 264 continues to slide along the side of post 260 as the device is expanded to a maximum degree illustrated in FIG. 35C. When the expansion force is relaxed, any substantial movement of post 260 towards the contracted position is blocked by ratchet finger 264, as illustrated in FIG. 35D. As post 260 attempts to move towards its contracted state, engagement end 260 is pressed firmly into interfering engagement with the side of post 260. Additionally, support surface 270 limits the movement of ratchet finger 264 in the contracting direction. The side wall of post 260 may comprise teeth or other interfering features that aid in preventing movement of post 260 back towards the contracted state.

Another exemplary locking mechanism 272 is illustrated in FIGS. 36A-36D. In this embodiment, a fork ratchet 274 is formed in the expandable device, such as in the wall of an expandable tubular. Fork ratchet 274 comprises a pair of prongs 276 that each have a divergent end 278. In the contracted state, prongs 276 are received in an opening 280 having a generally hourglass shape profile. In other words, divergent ends 278 reside in a divergent or expanded portion 282 of opening 280 and must be pulled through a narrow or constricted portion 284 when the device is expanded.

Figure 36A:
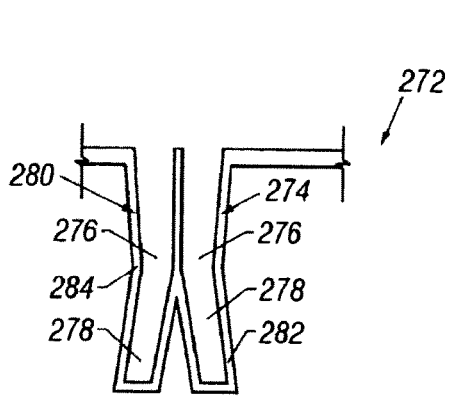
FIGS. 36 A-D illustrate another embodiment of the locking mechanism of FIG. 35.
Figure 36B:
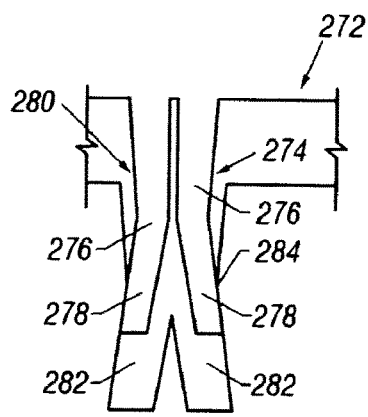
Figure 36C:
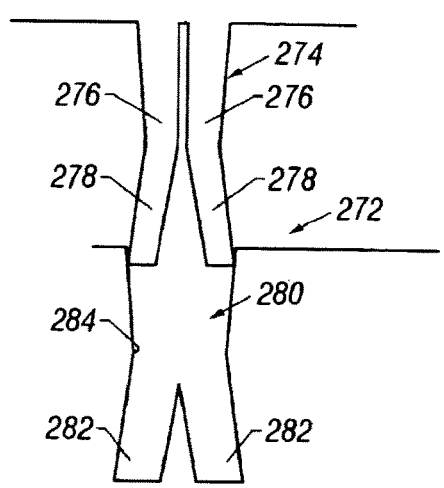
Figure 36D:
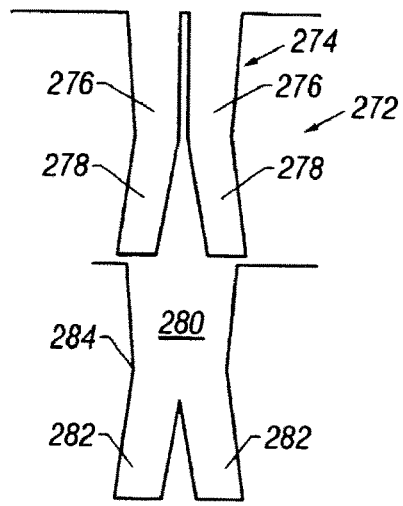

During expansion of the tubular or other device, divergent portions 282 are drawn through constricted region 284 (see FIGS. 36B and 36C.) Once prongs 276 are drawn clear of opening 280, the divergent portions 282 once again spring outwardly to their normal position. In this position, divergent portions 282 are wider than the entrance to opening 280, and fork ratchet 274 is prevented from reentering opening 280. Thus, the overall device is held in its expanded state.

Figure 37:
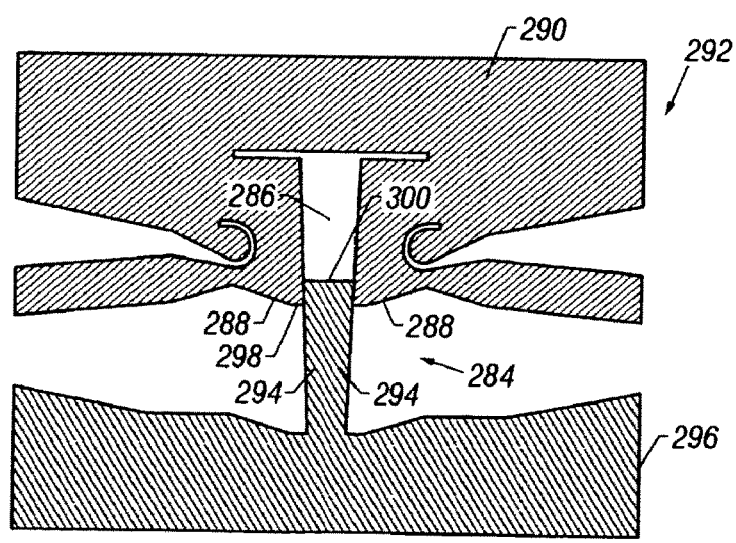
FIG. 37 illustrates a locking mechanism combined with an expandable cell.

Another exemplary locking mechanism 284 is illustrated in FIG. 37. Locking mechanism 284 is designed for use with horn style cells. In the specific example illustrated, a slot 286 is formed between a pair of spring member horns 288 within a thick strut 290 of an expandable cell 292. A wedge 294 extends from an adjacent thick strut 296 into slot 286. As cell 292 is expanded, wedge 294 is drawn outwardly through slot 286. The size of the wedge tip 298 and slot outlet 300 are selected to interfere when cell 292 is in its expanded state. This prevents flexing of horns 288 towards slot 286 and thereby inhibits collapse of the expanded cell.

Referring generally to FIGS. 38A-41B, a variety of expandable cell and locking mechanism combinations are illustrated. With specific reference to FIGS. 38A and 38B, one embodiment of an expandable cell 302 comprises thick struts 304 that are coupled together by thin struts 306 via spring members 308. Each thick strut 304 comprises one or more, e.g. two, ratchet fingers 310 that slide along a corresponding ratchet surface 312 formed on expanded regions of the thin struts 306 (see FIG. 38B).

Figure 38A:
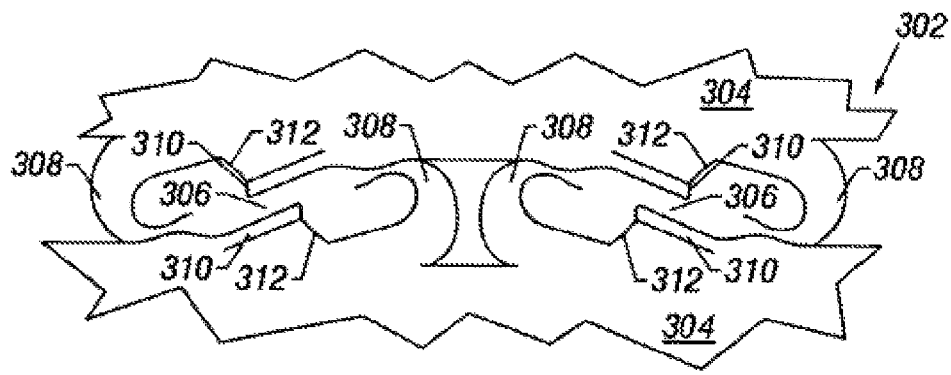
FIG. 38A-B illustrate an expandable cell combined with a locking mechanism in a collapsed and expanded position, respectively.
Figure 38B:
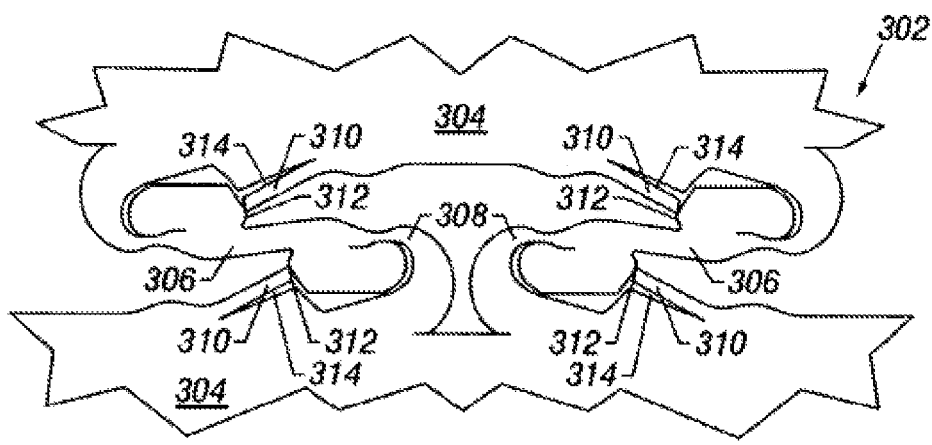

Ratchet surface 312 may incorporate ratchet teeth to engage the end of the corresponding ratchet finger 310. As the expandable cell 302 is transitioned from its contracted state, as illustrated in FIG. 38A, to an expanded state, as illustrated in FIG. 38B, ratchet fingers 310 are flexed away from a support surface 314 while sliding along corresponding ratchet surfaces 312. The ends of the ratchet fingers 310 do not allow sliding motion of corresponding ratchet surfaces 312 back towards the contracted state. Furthermore, support surfaces 314 may be relied on to limit any flexing of fingers 310 back towards the contracted position. Thus, when the expandable cell is in its expanded state, each of the ratchet fingers 310 acts against a corresponding ratchet surface 312 to support the cell against collapse.

Figure 39:
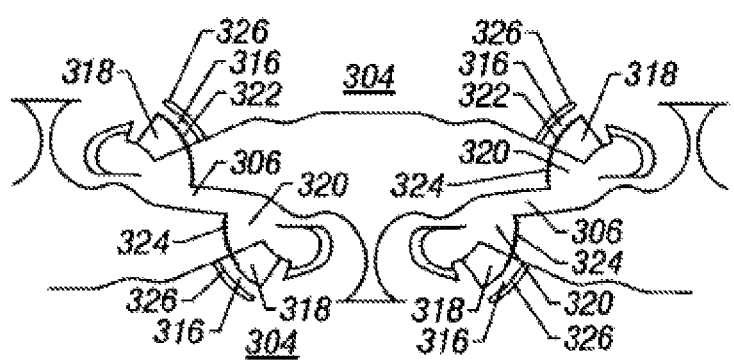
FIG. 39 illustrates an expandable cell with another embodiment of a locking mechanism.

Another embodiment of the system is illustrated in FIG. 39 and utilizes fingers in the form of ratchet pawls 316. In this embodiment, each ratchet pawl is formed in an appropriate thick strut 304 by creating an open area 318 configured to receive a corresponding portion 320 of thin strut 306 when in the contracted position. Each ratchet pawl 316 may comprise a plurality of teeth 322 positioned to engage corresponding teeth 324 extending from portion 320. Additionally, a relief cut 326 may be formed along ratchet pawl 316 generally opposite open area 318. Relief cut 326 allows ratchet pawl 316 to flex as teeth 322 are dragged past teeth 324 during transition of the cell from a contracted state to an expanded state. Teeth 322 and 324 are designed to prevent closure of the cell once expansion begins. Thus, the ratchet pawl 316 effectively ratchets along portion 320 holding the cell at each additional degree of expansion. As an alternative to teeth, the ratchet pawl 316 and cooperating portion 320 may utilize other types of interfering features to prevent contraction of the cell.

Figure 40A:
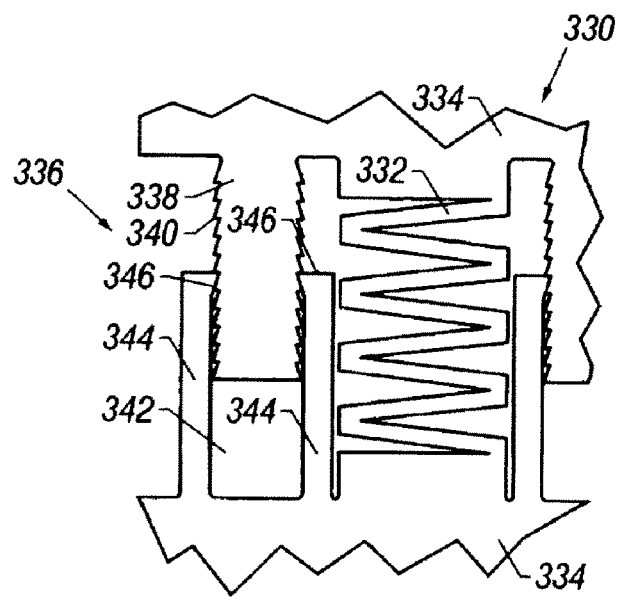
FIGS. 40 A-B illustrate an individual expandable cell and a plurality of expandable cells, respectively, combined with corresponding locking mechanisms.
Figure 40B:
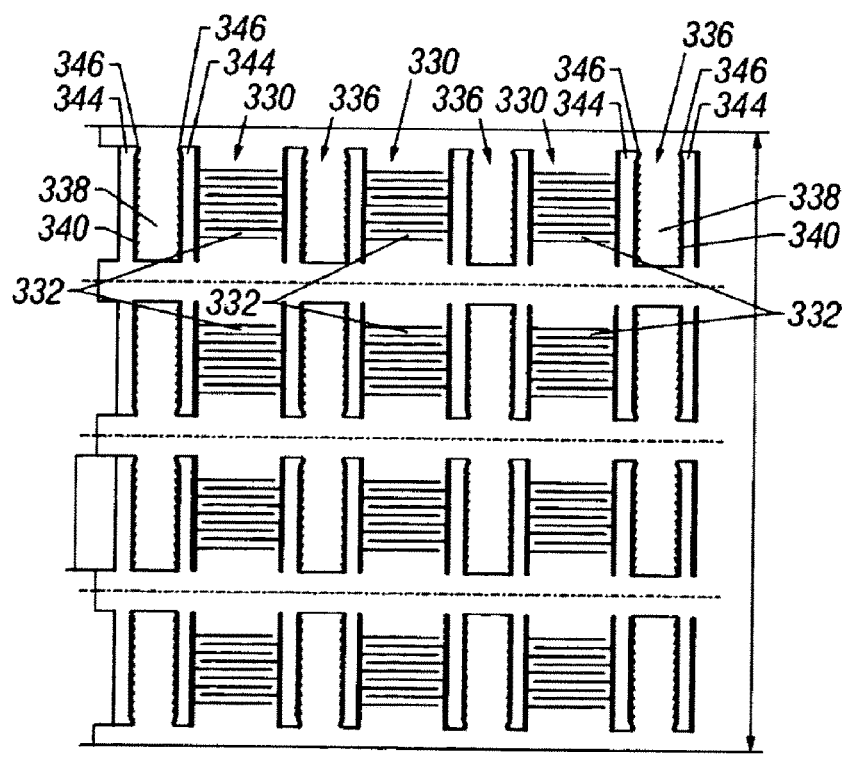

The locking mechanisms also may be used in cooperation with expandable cells that are not necessarily bistable cells. For example, in FIG. 40A an expandable cell 330 comprises a thin strut 332 disposed in an expandable "wishbone" type configuration between the thick struts 334 to which it is connected. A locking mechanism 336 cooperates with one or more of the expandable thin struts 332 to hold the expandable cells 330, at an expanded position. As illustrated in FIG. 40B, a locking mechanism 336 may be combined with each expandable cell 330, or there may be multiple expandable cells for each locking mechanism 336.

In this embodiment, locking mechanism 336 comprises a post 338 having external teeth 340. Post 338 is slidably received within an opening 342 defined by one or more flexible fingers 344 having engagement tips 346 that engage teeth 340. Fingers 344 flex outwardly to allow teeth 340 to slide past engagement tips 346 as the cell is expanded, but engagement tips 346 prevent post 338 from moving in a direction towards the contracted state. Thus, once expandable cell 330 is expanded, locking mechanism 336 prevents contraction of the cell.

Figure 41A:
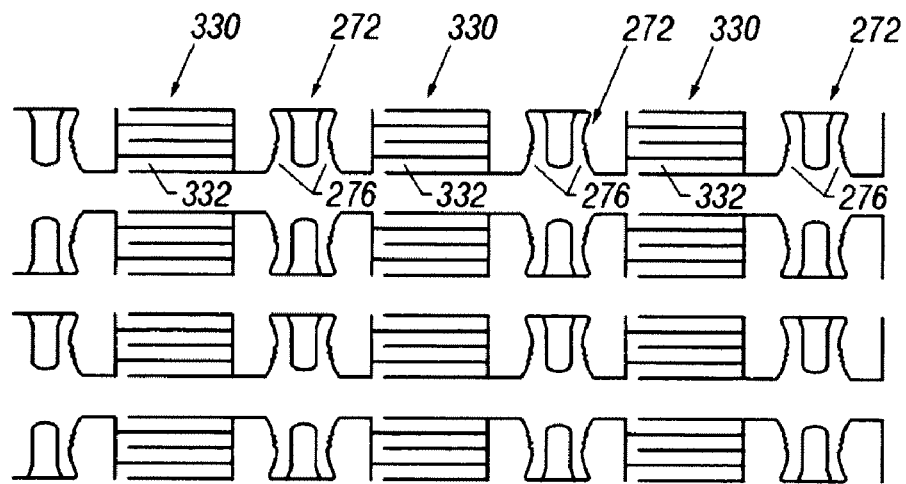
FIGS. 41 A-B illustrate another embodiment of combined expandable cells and locking mechanisms in collapsed and expanded positions, respectively.
Figure 41B:
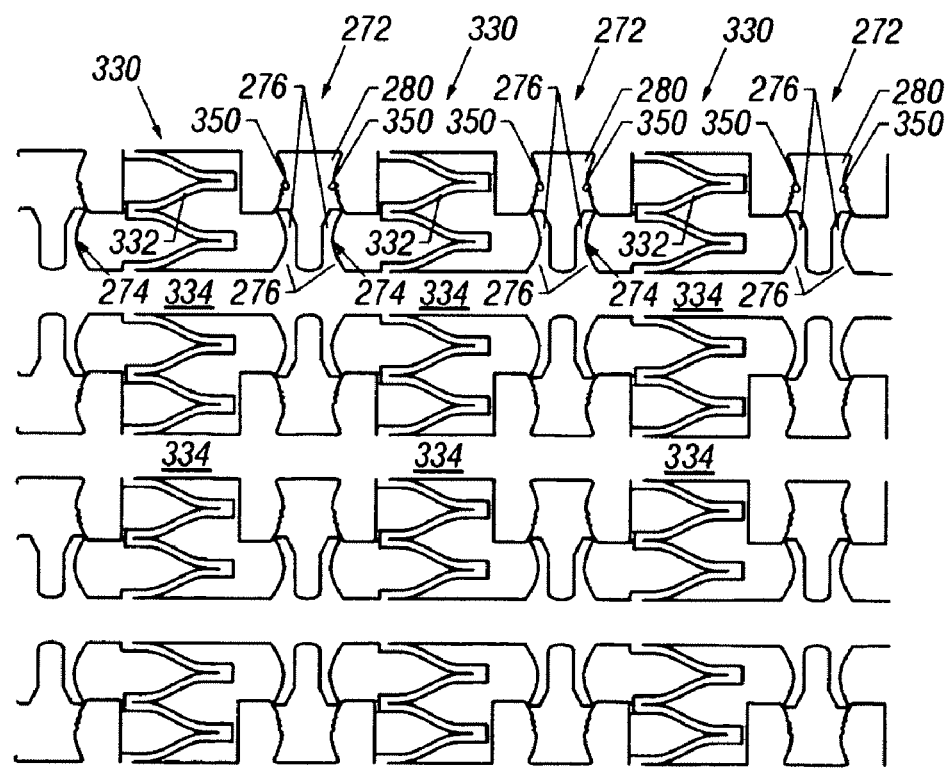

A similar design is illustrated in FIGS. 41A and 41B. This design combines the expandable cell described with reference to FIG. 40A and a locking mechanism of the type described in FIGS. 36A-36D. Thus, as the plurality of expandable cells 330 are moved from the contracted state illustrated in FIG. 41A to the expanded state illustrated in FIG. 41B, the wishbone style thin strut is expanded. Simultaneously, prongs 276 are pulled from their corresponding opening 280 to a position that prevents reentry of fork 274 into opening 280. The locking mechanism may be designed such that prongs 276 are withdrawn from and blocked from reentering opening 280. Alternatively, prongs 276 may be designed for interference with corresponding teeth or other interfering features 350 disposed along the outer limit of each opening 280 to prevent return movement of prongs 276 into opening 280.

Figure 42:
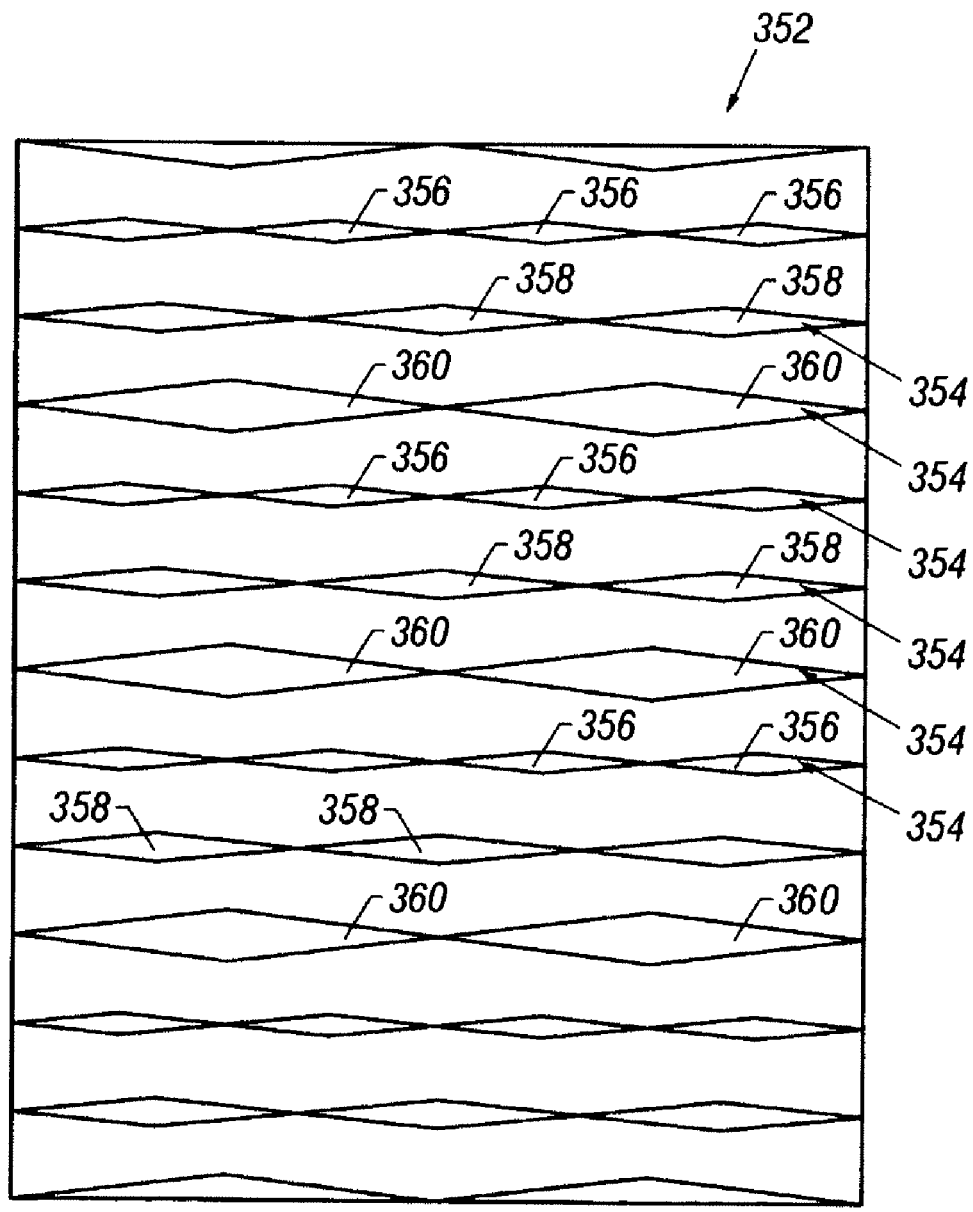
FIG. 42 is a schematic representation of the combination of expandable cells having differing sizes and configurations in a single expandable device.

It also should be noted that expandable devices, such as expandable tubulars, can be formed with a variety of cells and locking mechanisms having differing configurations, such as changes in size or type, as illustrated schematically in FIG. 42. For example, by stacking cells of different length or eccentric offset in a sheet or tube, it is possible to design an opening bias into the structure. The expandable device may be designed to allow certain rows of cells to open prior to other rows of cells or for the cells to open in a predetermined pattern or at a predetermined rate. In FIG. 42, for example, an expandable device 352 comprises rows of expandable cells 354. However, different rows 354 have cells of differing lengths, e.g. cells 356, 358 and 360. This allows certain rows of cells to open prior to adjoining rows of cells, because, at least with certain cell designs, the length of the cell affects the force required to expand the cell. Incorporating different rows of cells into an expandable device allows the user to know the rate of expansion for a given deployment force and facilitates the design of devices having cells which open in a predetermined sequence. Additionally, the use of different types of cells can improve compliance of the expandable device when the deployment force is not uniform along the length of the device.

It will be understood that the foregoing description is of exemplary embodiments of this invention, and that the invention is not limited to the specific forms shown. For example, the expandable cells can be combined into a variety of tubulars and other expandable structures; the size and shape of the expandable cells and locking mechanisms can be adjusted; the types of material utilized can be changed depending on the specific application; and a variety of mechanisms may be used to expand the cells. Also, the various cells can be formed by a variety of techniques including laser cutting, jet cutting, water jet cutting and other formation techniques. These and other modifications may be made in the design and arrangement of the elements without departing from the scope of the invention as expressed in the appended claims.

The invention claimed is:

1. An expandable device for use in a well bore, comprising:
    a first tubular expansion member being movable between a contracted state and an expanded state and having a plurality of cells that are expandable from a closed position to an open position, each cell having a thin strut coupled to a thick strut, wherein the thin strut is coupled to the thick strut at both ends of the cell;

a second tubular expansion member also being movable between a contracted state and an expanded state and having a plurality of cells that are expandable from a closed position to an open position, each cell having a thin strut coupled to a thick strut, wherein the thin strut is coupled to the thick strut at both ends of the cell; and an expandable connector interposing and coupled to the first and second tubular expansion members, the expandable connector being movable between contracted and expanded states with the first and second tubular expansion members to thereby form a string of tubular expansion members, wherein the first and second tubular expansion members do not overlap each other, wherein the plurality of cells of one or both of the first and second tubular expansion members are configured in rows about the respective tubular expansion member such that the rows alternate between at least two cell sizes.

2. The expandable device of claim 1, wherein the plurality of cells of at least one of the first and second tubular expansion members comprise bistable cells.

3. The expandable device of claim 2, wherein the expandable connector comprises a plurality of bistable cells having at least one thin strut coupled to a thick strut.

4. The expandable device of claim 1, wherein the expandable connector has a diameter greater than a diameter of each of the first and second tubular expansion members and is mechanically attached to an outer surface of each of the first and second tubular expansion members.

5. The expandable device of claim 1, wherein the expandable connector has a diameter lesser than a diameter of each of the first and second tubular expansion members and is mechanically attached to an inner surface of each of the first and second tubular expansion members.

6. The expandable device of claim 1, wherein axially adjacent ends of each of the first and second tubular expansion members is machined so as to define corresponding annular recesses for the receipt of the expandable connector, such that a flush-type connection is made between the first and second tubular expansion members.

7. The expandable device of claim 6, wherein the annular recess of each of the first and second tubular expansion members is defined on corresponding outer surfaces of each of the first and second tubular expansion members.

8. The expandable device of claim 6, wherein the annular recess of each of the first and second tubular expansion members is defined on corresponding inner surfaces of each of the first and second tubular expansion members.

9. The expandable device of claim 1, wherein expansion of the first and second tubular expansion members and the expandable connector is reversible and repeatable.

10. The expandable device of claim 1, wherein the at least two cell sizes comprise a first cell size having a first axial length along the tubular expansion member and a second cell size having a second axial length along the tubular expansion member.

11. The expandable device of claim 10, wherein the first cell size is configured to expand prior to the second cell size when the respective tubular expansion member moves from the contracted state to the expanded state.

12. The expandable device of claim 10, an axial length of the expandable connector is constant for the closed position and the open position.

13. The expandable device of claim 1, wherein the expandable connector has a plurality of cells that are expandable from a closed position to an open position.

14. The expandable device of claim 13, wherein the plurality of cells of the expandable connector comprise bistable cells.

15. A method comprising:
conveying an expandable device into a well bore with a conveyance device, the expandable device comprising:
a first tubular expansion member being movable between a contracted state and an expanded state and having a plurality of cells that are expandable from a closed position to an open position, each cell having a thin strut coupled to a thick strut, wherein the thin strut is coupled to the thick strut at both ends of the cell;
a second tubular expansion member also being movable between a contracted state and an expanded state and having a plurality of cells that are expandable from a closed position to an open position, each cell having a thin strut coupled to a thick strut, wherein the thin strut is coupled to the thick strut at both ends of the cell; and
an expandable connector interposing and coupled to the first and second tubular expansion members, the expandable connector being movable between contracted and expanded states with the first and second tubular expansion members to thereby form a string of tubular expansion members; and
deploying the expandable device in the well bore with a deployment device,
wherein the first and second tubular expansion members do not overlap each other,
wherein the plurality of cells of one or both of the first and second tubular expansion members are configured in rows about the respective tubular expansion member such that the rows alternate between at least two cell sizes.

16. The method of claim 15, wherein the conveyance device is a wireline cable, a coiled tubing, a coiled tubing with wireline conductor, a drill pipe, a tubing, or a casing.

17. The method of claim 15, wherein the deployment device is an inflatable packer element, a mechanical packer element, an expandable swage, a piston apparatus, a mechanical actuator, an electrical solenoid, a plug type apparatus, a ball type apparatus, or a rotary type expander.

* * * * *